US010368831B2

(12) United States Patent
Duric et al.

(10) Patent No.: US 10,368,831 B2
(45) Date of Patent: Aug. 6, 2019

(54) WAVEFORM ENHANCED REFLECTION AND MARGIN BOUNDARY CHARACTERIZATION FOR ULTRASOUND TOMOGRAPHY

(71) Applicant: Delphinus Medical Technologies, Inc., Novi, MI (US)

(72) Inventors: Nebojsa Duric, Novi, MI (US); Peter J. Littrup, Novi, MI (US); Gursharan Singh Sandhu, Novi, MI (US); Mark Krycia, Novi, MI (US); Mark Sak, Novi, MI (US)

(73) Assignee: Delphinus Medical Technologies, Inc., Novi, MI (US)

( * ) Notice: Subject to any disclaimer, the term of this patent is extended or adjusted under 35 U.S.C. 154(b) by 0 days.

(21) Appl. No.: 15/829,748

(22) Filed: Dec. 1, 2017

(65) Prior Publication Data
US 2018/0153502 A1 Jun. 7, 2018

Related U.S. Application Data

(60) Provisional application No. 62/429,563, filed on Dec. 2, 2016, provisional application No. 62/429,542, filed on Dec. 2, 2016.

(51) Int. Cl.
*A61B 8/13* (2006.01)
*A61B 8/08* (2006.01)
(Continued)

(52) U.S. Cl.
CPC ............ *A61B 8/0825* (2013.01); *A61B 8/085* (2013.01); *A61B 8/13* (2013.01); *A61B 8/15* (2013.01);
(Continued)

(58) Field of Classification Search
CPC .......... G06T 2207/10136; G06T 5/008; A61B 8/0825; A61B 8/085; A61B 8/13; A61B 8/406; A61B 8/5207
See application file for complete search history.

(56) References Cited

U.S. PATENT DOCUMENTS 8,663,113 B2  3/2014  Schmidt et al.
9,113,835 B2  8/2015  Li
(Continued)

FOREIGN PATENT DOCUMENTS

WO  WO-2017040866 A1  3/2017
WO  WO-2017139389 A1  8/2017

OTHER PUBLICATIONS

PCT/US17/64350 International Search Report and Written Opinion dated Mar. 22, 2018.

*Primary Examiner* — Mark D Remaly
(74) *Attorney, Agent, or Firm* — Wilson Sonsini Goodrich & Rosati

(57) ABSTRACT

The present invention provides improved methods and systems for generating enhanced images of a volume of tissue. In an aspect, the method comprises receiving from a transducer, a plurality of acoustic signals derived from acoustic waveforms transmitted through the volume of tissue; generating from the acoustic signals, a first reflection rendering that characterizes sound reflection, the first reflection rendering comprising a first distribution of reflection values across a region of the volume of tissue; generating from the acoustic signals, a sound speed rendering that characterizes sound speed, the sound speed rendering comprising a distribution of sound speed values across the region; generating from the sound speed rendering, a second reflection rendering that characterizes sound reflection, the second reflection rendering comprising a second distribution of reflection
(Continued)

values across the region; and rendering one or more combined images, based on the first reflection rendering and the second reflection rendering.

28 Claims, 16 Drawing Sheets

(51) Int. Cl.
*A61B 8/00* (2006.01)
*G06T 5/00* (2006.01)
*A61B 8/15* (2006.01)

(52) U.S. Cl.
CPC ............ *A61B 8/406* (2013.01); *A61B 8/5207* (2013.01); *A61B 8/5253* (2013.01); *G06T 5/008* (2013.01); *G06T 2207/10136* (2013.01)

(56) References Cited

U.S. PATENT DOCUMENTS

| | | |
|---|---|---|
| 2011/0201932 A1 | 8/2011 | Duric et al. |
| 2013/0204136 A1 | 8/2013 | Duric et al. |
| 2013/0204137 A1 | 8/2013 | Roy et al. |
| 2013/0251222 A1 | 9/2013 | Huang |
| 2014/0018682 A1* | 1/2014 | Baba .................. A61B 8/483 600/443 |
| 2014/0066772 A1 | 3/2014 | West et al. |
| 2014/0276068 A1 | 9/2014 | Szpak et al. |
| 2015/0313577 A1 | 11/2015 | Duric et al. |
| 2016/0022245 A1 | 1/2016 | Tesic et al. |
| 2016/0030000 A1 | 2/2016 | Sandhu et al. |
| 2016/0038123 A1 | 2/2016 | Duric et al. |
| 2016/0317121 A1 | 11/2016 | Frenz et al. |

* cited by examiner

Figure 10A. Top: Coronal UST sound speed images for 6 different patients. Bottom: Corresponding fat subtracted contrast enhanced MR images.

Figure 10B. The spatial resolution of each modality was estimated using profile cuts of thin features using, the full-width, half-maximum criterion, as illustrated.

WAVEFORM ENHANCED REFLECTION AND MARGIN BOUNDARY CHARACTERIZATION FOR ULTRASOUND TOMOGRAPHY

CROSS-REFERENCE

This application claims the benefit of provisional patent application U.S. Prov. Ser. App. No. 62/429,542, filed Dec. 2, 2016, entitled "Waveform Enhanced Reflection for Ultrasound Tomography", and U.S. Prov. Ser. App. No. 62/429,563, filed Dec. 2, 2016, entitled "Margin Boundary Characterization and Region of Interest Diagnostics for Ultrasound Tomography", which are each incorporated herein by reference in their entirety.

The subject matter of this application is related to the following patent applications: U.S. patent application Ser. No. 14/817,470 entitled "Method for Generating an Enhanced Image of A Volume of Tissue"; U.S. patent application Ser. No. 14/819,091 entitled "Ultrasound Waveform Tomography Method and System"; and P.C.T. International App. Pub. No. WO2017040866 entitled "Tissue Imaging and Analysis Using Ultrasound Waveform Tomography", which are each incorporated herein by reference in their entirety.

STATEMENT AS TO FEDERALLY SPONSORED RESEARCH

This invention was made with the support of the United States government under Grant number R44 CA165320 by National Cancer Institute. The Government has certain rights in the invention.

BACKGROUND OF THE INVENTION

Current methods for ultrasound reflection imaging can be less than ideal in some respects. For example, current methods for ultrasound reflection imaging may be based on the coherent summation of pulse echo signals. While methods based on a pulse echo approach work well in breasts dominated by fatty tissues, there may be limitations when imaging dense breasts. These limitations may arise from (i) loss of signal coherency when illuminating large tissue volumes (e.g., patient motion), (ii) loss of coherency arising from multiple scattering events in dense breast tissue, (model mismatch) and/or (iii) inability to penetrate deep into dense highly attenuating tissue.

Conventional techniques for imaging and diagnosing breast and other types of cancer such as, for example, mammography, magnetic resonance imaging (MRI), or ultrasound can be less than ideal in at least some respects. For example, MRI can be prohibitively expensive for routine use. In another example, mammography involves ionizing radiation, which may limit frequency of patient screening, and may lack specificity in identifying various types of masses such as, for example, more deadly, invasive carcinomas and/or less deadly Ductal Carcinomas in situ. Such a lack of specificity may result in excessive patient biopsies and/or initial misdiagnoses. Additionally, mammography may have low sensitivity in patients with dense breast tissue resulting in missed deadly invasive cancers. In an additional example, the efficacy of conventional ultrasound techniques in imaging and diagnosing cancer may be limited by the skill of the operator. Additionally, conventional ultrasound may not be optimally configured or employed to image a whole organ, with sufficient resolution and/or image quality to sufficiently differentiate various types of tissue or to correctly give a diagnosis.

In light of the above, imaging and diagnostic methods which improve quality of tissue imaging and specificity of mass characterization may be needed. Ideally, such methods may provide enhanced image quality (e.g., with high resolution) through an imaging modality that is inexpensive and does not use ionizing radiation (e.g., ultrasound imaging), thereby enabling accurate identification and classification of various types of breast masses with sufficient clinical sensitivity and specificity.

SUMMARY OF THE INVENTION

Recognizing a need for high-quality imaging of tissue, the present disclosure provides improved methods and systems for enhancing a reflection image of a volume of tissue. Conventional reflection imaging, such as envelope detection (ERF) imaging, provides echo contrast for detection and characterization of lesions. Another method, REF imaging (raw RF signals), helps define margins and cancer-specific spiculations and architectural distortion. Embodiments of the present disclosure provide the use of waveform reconstruction which may leverage the benefits of both ERF imaging and REF imaging, while mitigating the limitations of conventional methods noted above. Such mitigation may be made possible by waveform's ability to account for multiple scatters and provide deep penetration (by virtue of the lower frequencies used) while maintaining high spatial resolution.

The methods described herein, by which waveform data can be added to pulse-echo data, may utilize acoustic impedance information gathered from sound speed images. Since changes in acoustic impedance may yield reflections, the method may use the gradient of the sound speed image to calculate reflection information. The low frequencies (~1 MHz) associated with the sound speed waveform reconstructions may provide information on specular reflections (down to ~1 mm). Since pulse echo imaging may occur at higher frequencies (~1 to 5 MHz), the latter may be better able to image the sub-mm granularity that provides information on speckle patterns.

Since RF signals may represent the native reflections (highlighting tissue edges) and may provide the most flexibility for further manipulation and conditioning, the methods disclosed herein provide a means to combine the contribution from the REF images with the waveform component. Such a method may preserve high spatial resolution and sensitivity to edges while additionally preserving the general appearance of a reflection image. Additionally, the methods disclosed herein may sufficiently improve image quality for accurate mass detection, and encourage mass discrimination to avoid unnecessary patient biopsies.

An aspect of the present disclosure provides improved methods for high-specificity characterization of breast tissue based on classifier models which identify a region of interest and develop prognostic parameters, which prognostic parameters comprise measurements of sound propagation interior to and exterior to the region of interest, qualitative assessments of the tumor morphology (e.g., the shape of the boundary of the region of interest), and semi-quantitative parameters (e.g., a score on an integer scale of the margin boundary). The methods disclosed herein may sufficiently improve specificity of mass characterization, which methods encourage mass discrimination to avoid excessive patient biopsies.

Another aspect of the present disclosure provides a method for generating an enhanced image of a volume of tissue, which method is implemented by a computer comprising one or more processors and computer readable media comprising instructions. The method may comprise: receiving from a transducer, a plurality of acoustic signals derived from acoustic waveforms transmitted through the volume of tissue, wherein the transducer comprises an array of ultrasound transmitters and an array of ultrasound receivers configured to surround the volume of tissue; generating from the plurality of acoustic signals, a first reflection rendering that characterizes sound reflection, the first reflection rendering comprising a first distribution of reflection values across a region of the volume of tissue; generating from the plurality of acoustic signals, a sound speed rendering that characterizes sound speed, the sound speed rendering comprising a distribution of sound speed values across the region of the volume of tissue; generating from the sound speed rendering, a second reflection rendering that characterizes sound reflection, the second reflection rendering comprising a second distribution of reflection values across the region of the volume of tissue; and rendering one or more combined images, in response to the first reflection rendering and the second reflection rendering, thereby generating the enhanced image of the volume of tissue.

In some embodiments, the enhancement comprises an increase in resolution of the image from greater than about 1 mm to less than about 0.7 mm. In some embodiments, the enhancement comprises an increase in contrast of the image from a factor of at least about 2 to a factor of at least about 10. In some embodiments, the enhancement comprises an increase in conspicuity of lesions in the volume of tissue from a factor of at least about 2 to a factor of at least about 10. In some embodiments, the enhancement comprises an increase in specificity of lesion characterization in the volume of tissue such that the specificity is at least about 75% to at least about 95%. In some embodiments, the tissue comprises breast tissue.

In some embodiments, the volume of tissue comprises a distribution of one or more of: fat tissue, parenchymal tissue, cancerous tissue, and abnormal tissue. In some embodiments, the fat tissue comprises fatty parenchyma, parenchymal fat, or subcutaneous fat. In some embodiments, the abnormal tissue comprises fibrocystic tissue or a fibroadenoma. In some embodiments, generating the first reflection rendering comprises generating a plurality of acoustomechanical parameter slices associated with a plurality of coronal slices through the volume of tissue. In some embodiments, generating the first reflection rendering comprises generating a distribution of acoustic reflection signals, wherein the acoustic reflection signals characterize a relationship between reflected intensities and emitted intensities of the acoustic waveforms, wherein the relationship is selected from the group consisting of a sum, a difference, and a ratio. In some embodiments, generating the first reflection rendering comprises generating a distribution of acoustic reflection signals, wherein the acoustic reflection signals characterize a change in acoustic impedance of the volume of tissue. In some embodiments, generating the first reflection rendering comprises generating a distribution of acoustic reflection signals received from a first array of transducers, the first array of transducers transmitting and receiving at a first frequency greater than a second frequency of a second array of transducers used to generate the sound speed rendering. In some embodiments, generating the first reflection rendering comprises generating a distribution of acoustic reflection signals received from a first array of transducers, the first array of transducers transmitting and receiving at a first frequency less than a second frequency of a second array of transducers used to generate the sound speed rendering. In some embodiments, generating the sound speed rendering comprises generating a plurality of acoustomechanical parameter slices associated with a plurality of coronal slices through the volume of tissue. In some embodiments, the sound speed rendering comprises a real portion corresponding to a phase velocity, and an imaginary portion corresponding to a sound attenuation.

In some embodiments, generating the sound speed rendering comprises generating an initial sound speed rendering based on simulated waveforms according to a time travel tomography algorithm, and the initial sound speed rendering is iteratively optimized until ray artifacts are reduced to a pre-determined threshold. In some embodiments, the simulated waveforms are optimized for each of a plurality of sound frequency components. In some embodiments, generating the second reflection rendering comprises calculating a gradient of the sound speed rendering. In some embodiments, calculating the gradient comprises performing one or more algorithms selected from the group consisting of the Sobel-Feldman operator, the Scharr operator, the Prewitt operator, and the Roberts Cross operator. In some embodiments, calculating generating a second reflection rendering comprises performing computational relations selected from the group consisting of averaging, truncation, normalization, smoothing, addition, subtraction, multiplication, and division. In some embodiments, smoothing comprises convolution with another function, adjacent averaging, or Fourier filtering.

In some embodiments, rendering the one or more combined images comprises performing an element-wise average or a weighted average of the first reflection rendering and the second reflection rendering. In some embodiments, rendering the one or more combined images comprises performing an element-wise sum or a weighted sum of the first reflection rendering and the second reflection rendering. In some embodiments, rendering the one or more combined images comprises performing an element-wise product or a weighted product of the first reflection rendering and the second reflection rendering. In some embodiments, rendering the one or more combined images comprises performing a convolution of the first reflection rendering and the second reflection rendering. In some embodiments, rendering the one or more combined images comprises performing computational relations on the first reflection rendering and/or the second reflection rendering, the computational relations selected from the group consisting of averaging, truncation, normalization, smoothing, addition, subtraction, multiplication, and division.

In some embodiments, the method further comprises classifying, based on the one or more combined images, different types of lesions in the volume of tissue as at least one of a cancerous tumor, a fibroadenoma, a cyst, a non-specific benign mass, and an unidentifiable mass.

In some embodiments, the present disclosure provides a non-transitory computer-readable storage medium with instructions stored thereon that, when executed by a processor, cause a processor to perform the disclosed method.

In some embodiments, the present disclosure provides a system for generating enhanced images of a volume of tissue. The system may comprise: a transducer array comprising an array of ultrasound emitters and an array of ultrasound receivers, the transducer array configured to surround a volume of tissue, wherein the array of ultrasound transmitters is configured to emit acoustic waveforms toward the volume of tissue, wherein the array of ultrasound receivers is configured to receive the emitted acoustic waveforms and convert the received acoustic waveforms to a plurality of acoustic signals; a processor comprising a computer readable medium configured with instructions, that when executed, cause the processor to perform the disclosed method; and a display visible to a user configured to display the one or more combined images.

Another aspect of the present disclosure provides a method for characterizing a volume of breast tissue of a patient. The method may comprise: receiving from a transducer, a plurality of acoustic signals derived from acoustic waveforms transmitted through the volume of tissue, wherein the transducer comprises an array of ultrasound transmitters and an array of ultrasound receivers configured to surround the volume of tissue; generating from the plurality of acoustic signals, a three-dimensional acoustic rendering that characterizes sound propagation within the volume of tissue; receiving input from a user corresponding to a user-selected region of interest; generating from the acoustic rendering a first plurality of prognostic parameters corresponding to sound propagation interior to the user-selected region of interest; generating from the acoustic rendering a second plurality of prognostic parameters corresponding to sound propagation exterior to the user-selected region of interest; and characterizing a lesion within the volume of tissue using the first plurality of interior prognostic parameters and the second plurality of exterior prognostic parameters.

In some embodiments, the three-dimensional acoustic rendering comprises an acoustic attenuation rendering, an acoustic reflection rendering, and an acoustic sound speed rendering. In some embodiments, the method further comprises generating a merged three-dimensional rendering of the acoustic reflection rendering, the acoustic attenuation rendering, and the acoustic sound speed rendering. In some embodiments, the first plurality of prognostic parameters comprises a volume-average value of acoustic attenuation, a volume-average value of acoustic speed, and a volume-average value of acoustic reflectivity. In some embodiments, the second plurality of prognostic parameters comprises a volume-average value of acoustic attenuation, a volume-average value of acoustic speed, and a volume-average value of acoustic reflectivity. In some embodiments, the user-selected region of interest is selected from at least one of an acoustic attenuation rendering, an acoustic reflection rendering, and an acoustic sound speed rendering. In some embodiments, the user-selected region of interest is selected from the merged three dimensional rendering. In some embodiments, selection of the user-selected region of interest is aided or optimized by a computer-implemented algorithm.

In some embodiments, a lesion in the volume of tissue is classified as at least one of a cancerous tumor, a fibroadenoma, a cyst, a nonspecific benign mass, and an unidentifiable mass. In some embodiments, classifying a lesion in the volume of tissue comprises using a threshold value of the first plurality of prognostic parameters or the second plurality of prognostic parameters. In some embodiments, at least one prognostic parameter among the first plurality of prognostic parameters or the second plurality of prognostic parameters comprises a user-selected classification of a margin of the region of interest according to an integer scale. In some embodiments, at least one prognostic parameter among the first plurality of prognostic parameters or the second plurality of prognostic parameters comprises a difference between an acoustic parameter interior to the region of interest and an acoustic parameter exterior to the region of interest. In some embodiments, the first plurality of prognostic parameters comprises a volume-standard-deviation value of acoustic attenuation, a volume-average value of acoustic speed, and a volume-average value of acoustic reflectivity. In some embodiments, the first plurality of prognostic parameters comprises a volume-standard-deviation value of acoustic attenuation, a volume-average value of acoustic speed, and a volume-average value of acoustic reflectivity. In some embodiments, the specificity of classification of a lesion in the volume of tissue is increased such that the specificity is at least about 75% to at least about 95%.

In some embodiments, the present disclosure provides a system for generating enhanced images of a volume of tissue. The system may comprise: a transducer array comprising an array of ultrasound emitters and an array of ultrasound receivers, the transducer array configured to surround a volume of tissue, wherein the array of ultrasound transmitters is configured to emit acoustic waveforms toward the volume of tissue, wherein the array of ultrasound receivers is configured to receive the emitted acoustic waveforms and convert the received acoustic waveforms to a plurality of acoustic signals; a processor comprising a computer readable medium configured with instructions, that when executed, cause the processor to perform the disclosed method; and a display visible to a user configured to display the one or more combined images.

Another aspect of the present disclosure provides a method of breast ultrasound imaging and analysis. The method may comprise: scanning a breast with ultrasound tomography; determining a tumor sound speed and sound reflection based on the scanning; calculating a gradient of the tumor sound speed; determining a tumor sound reflectivity based on the gradient and a response to a radio frequency component of the sound reflection; and outputting an image of the breast based on the tumor sound reflectivity.

Another aspect of the present disclosure provides a method of breast ultrasound imaging and analysis. The method may comprise: scanning a breast with ultrasound tomography; determining a tumor sound speed, sound reflection, and sound attenuation based on the scanning; generating a reflection score based on the tumor sound speed and attenuation; characterizing mass margins of the breast based on the reflection score; and identifying a tumoral or peritumoral region of interest within the breast.

Another aspect of the present disclosure provides a non-transitory computer readable medium comprising machine-executable code that, upon execution by one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is intended to encompass "and/or" unless otherwise stated.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Reference throughout this specification to "one embodiment", "an embodiment", or "some embodiments" means that a particular feature, structure, or characteristic described may be included in at least one embodiment of the present invention, and each of these embodiments may be combined with other embodiments in accordance with the present disclosure. Thus, the appearances of the phrases "in one embodiment", "in an embodiment", or "in some embodiments" throughout this specification do not necessarily all refer to the same embodiment. Furthermore, the particular features, structures, or characteristics may be combined in any suitable manner in one or more embodiments.

Figure 1:
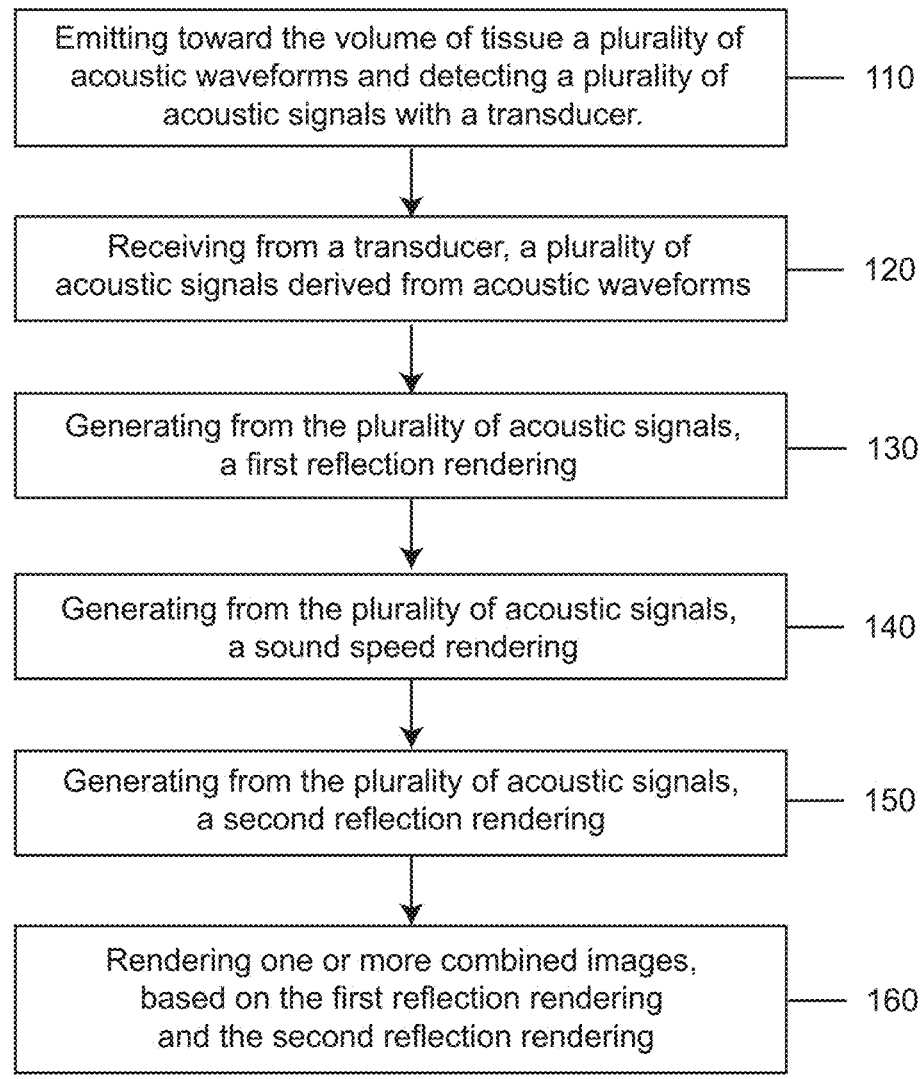
FIG. 1 shows a method of generating an enhanced image of a volume of tissue, in accordance with embodiments.

Embodiments of the present disclosure provide a method for generating an enhanced image of a volume of tissue. The method may be implemented by a computer comprising one or more processors and computer readable media comprising instructions to perform the method for generating an enhanced image of a volume of tissue. FIG. 1 shows an exemplary method 100 for generating an enhanced image of a volume of tissue, in accordance with some embodiments. The method 100 may comprise emitting toward the volume of tissue a plurality of acoustic waveforms and detecting from the volume of tissue a plurality of acoustic signals with a transducer. The transducer may comprise an array of ultrasound transmitters and an array of ultrasound receivers configured to surround the volume of tissue 110. The method 100 may further comprise receiving from a transducer, a plurality of acoustic signals derived from acoustic waveforms transmitted through the volume of tissue 120. The method 100 may further comprise generating from the plurality of acoustic signals, a first reflection rendering that characterizes sound reflection. The first reflection rendering may comprise a first distribution of reflection values across a region of the volume of tissue 130. The method 100 may further comprise generating from the plurality of acoustic signals, a sound speed rendering that characterizes sound speed. The sound speed rendering may comprise a distribution of sound speed values across the region of the volume of tissue 140. The method 100 may further comprise generating from the sound speed rendering, a second reflection rendering that characterizes sound reflection. The second reflection rendering may comprise a second distribution of reflection values across the region of the volume of tissue 150. The method 100 may further comprise rendering one or more combined images, based on the first reflection rendering and the second reflection rendering, thereby generating the enhanced image of the volume of tissue 160.

In some embodiments, method 100 may function to render ultrasound images that enhance target objects within a field of view, in order to facilitate characterization of the volume of tissue (e.g., a whole breast, another organ). Additionally or alternatively, the volume of tissue may comprise a distribution of one or more of: fat tissue (e.g., fatty parenchyma, parenchymal fat, subcutaneous fat, etc.), parenchymal tissue, cancerous tissue, abnormal tissue (e.g., fibrocystic tissue, fibroadenomas, etc.), and any other suitable tissue type within the volume of tissue.

Additionally or alternatively, method 100 may function to enhance the image resolution of a reflection image by up to 5 times (i.e., 5×), for example, within a range defined between any two of the following values: about 1.05×, about 1.1×, about 1.2×, about 1.5×, and about 5×. Additionally or alternatively, method 100 may function to enhance the image contrast of a reflection image by up to 10×, for example, within a range defined between any two of the following values: about 1.05×, about 1.1×, about 2×, about 5×, and about 10×. Additionally or alternatively, method 100 may function to enhance the conspicuity of lesions in a reflection image. Additionally or alternatively, method 100 may function to produce images that may be aligned with regulatory standards for medical imaging, as regulated, for instance, by the U.S. Food and Drug Administration (FDA). Method 100 may be used to characterize tissue of a human breast, but may additionally or alternatively be used to characterize tissue of an arm, leg, other appendage, and/or any suitable volume of tissue in a human or other animal. In relation to current ultrasound methods and systems, method 100 may improve sensitivity in detection of suspicious masses within acoustic reflection renderings, while providing specificity in characterization of types of masses. Such masses may include but are not limited to: a cancerous tumor, a fibroadenoma, a cyst, a nonspecific benign mass, and an unidentifiable mass. Method 100 may, however, function to enable diagnosis, monitoring, and/or characterization of a volume of tissue in any other suitable manner.

In some embodiments, method 100 may be used to generate one or more renderings that may be used to detect abnormalities (e.g., cancerous tissues) in a human or other animal. As such, in one variation, method 100 may be used to characterize the tissue to facilitate diagnoses of cancer, assess its type, and determine its extent (e.g., to determine whether a mass in the tissue may be surgically removable), or to assess risk of cancer development (e.g., measuring breast tissue density). In yet another embodiment, method 100 may be used to characterize and/or investigate particular aspects of the tissue, such as to determine whether a mass in the tissue may be a tumor, cyst, fibroadenoma, or other kind of mass. Method 100 may be used in any suitable application for imaging a volume of tissue or other suitable object. Method 100 may be implemented, at least in part, by way of an embodiment, variation, and/or example of the system 200 described in the section titled "Ultrasound Tomography System" below; however, method 100 may additionally or alternatively be implemented using any other suitable system.

While FIG. 1 shows a method of generating an enhanced image of a volume of tissue, in accordance with some embodiments, a person of ordinary skill in the art will recognize many adaptations and variations. Further, one or more steps shown in FIG. 1 may be deleted or repeated, additional steps can be added, and the steps can be performed in any order.

Emitting and Receiving Acoustic Signals

At a step 110 of the method 100, a plurality of acoustic waveforms may be emitted toward the volume of tissue, and a plurality of acoustic signals may be detected from the volume of tissue with a transducer. The transducer may comprise an array of ultrasound transmitters and an array of ultrasound receivers configured to surround the volume of tissue. At a step 120, a plurality of acoustic signals derived from acoustic waveforms transmitted through the volume of tissue may be received by a computer from a transducer. Steps 110 and 120 function to gather acoustic data from which renderings of the volume of tissue may be derived in other steps of the method 100. Emitting and detecting acoustic waveforms may comprise surrounding the volume of tissue with the array of ultrasound transmitters and/or with a ring transducer comprising the array of ultrasound transmitters. The acoustic waveforms may be characterized by frequencies of approximately 1 MHz, approximately 2 MHz, approximately 3 MHz, approximately 4 MHz, approximately 5 MHz, approximately 6 MHz, approximately 7 MHz, approximately 8 MHz, approximately 9 MHz, approximately 10 MHz, approximately 11 MHz, approximately 12 MHz, approximately 13 MHz, approximately 14 MHz, approximately 15 MHz, approximately 16 MHz, approximately 17 MHz, approximately 18 MHz, approximately 19 MHz, approximately 20 MHz, or any suitable frequency for medical imaging or other applications. The array of transmitters may comprise transducer elements configured to emit at a plurality of frequencies. Additionally or alternatively, an individual element in a transducer array may be configured to emit at one of a plurality of frequencies emitted by the array, such that the frequency of a transducer element may be optimized for a particular type of acoustic rendering.

The detected acoustic signals of step 110 may be derived from interactions between the emitted acoustic waveforms and the tissue, wherein interactions may comprise one or more of: scattering (e.g., reflection, refraction, diffraction, diffusion, etc.) and transmission of the acoustic waves through the tissue. The acoustic signals may travel along a straight, bent, zig-zag, or curved path, or a path of any suitable shape as determined by the physics of acoustic wave propagation. Detecting acoustic signals may comprise surrounding the volume of tissue with the array of ultrasound receivers and/or with a ring transducer comprising the array of ultrasound receivers. The acoustic signals may be characterized by frequencies of approximately 1 MHz, approximately 2 MHz, approximately 3 MHz, approximately 4 MHz, approximately 5 MHz, approximately 6 MHz, approximately 7 MHz, approximately 8 MHz, approximately 9 MHz, approximately 10 MHz, approximately 11 MHz, approximately 12 MHz, approximately 13 MHz, approximately 14 MHz, approximately 15 MHz, approximately 16 MHz, approximately 17 MHz, approximately 18 MHz, approximately 19 MHz, approximately 20 MHz, or any suitable frequency for medical imaging or other applications. The array of receivers may comprise transducer elements configured to emit at a plurality of frequencies. Additionally or alternatively, an individual transducer in an array may be configured to receive at one of a plurality of frequencies received by the array, such that the frequency of a transducer element may be optimized for a particular type of acoustic rendering.

At step 110 of the method 100, emitting acoustic waveforms and detecting a set of acoustic signals may be performed with an ultrasound tomographic scanner, for example, using methods similar to those described in U.S. Pat. Nos. 6,385,474; 6,728,567; 8,663,113; 8,876,716; and 9,113,835; and U.S. Publication Nos. 2013/0041261 and 2013/0204136, which are each incorporated by reference in their entirety. However, any suitable ultrasound device or scanner may be used.

Figure 2A:
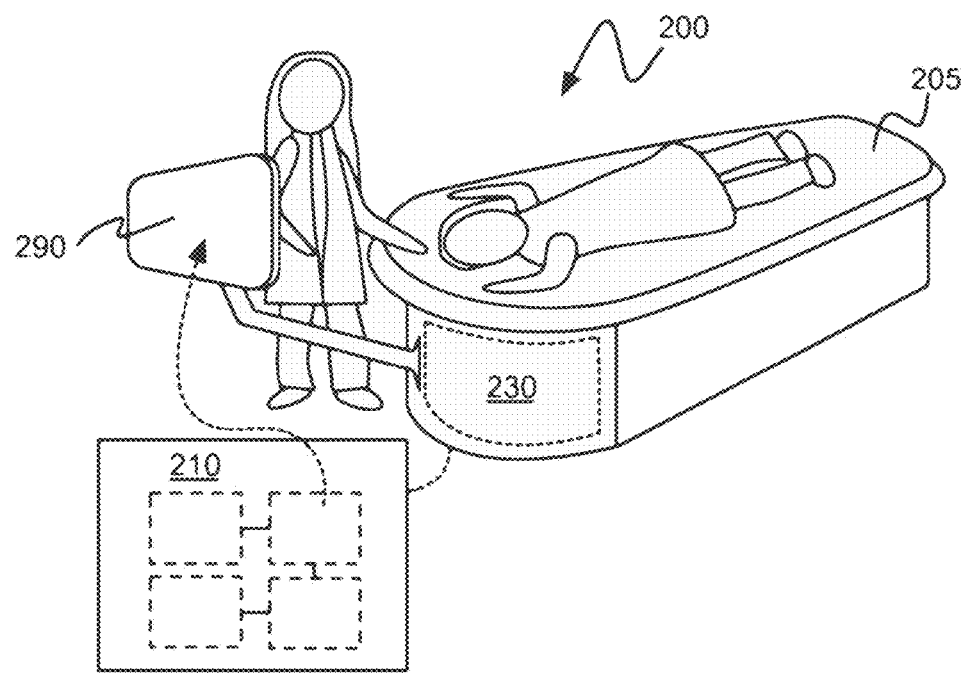
FIG. 2A is a schematic of an exemplary ultrasound scanner, in accordance with embodiments.

FIG. 2A shows a schematic of an exemplary ultrasound scanner 200, in accordance with embodiments. The ultrasound scanner may be used to emit acoustic waveforms and detect a set of acoustic signals, for example as discussed in FIG. 1. The steps of scanning the tissue and detecting acoustic signals may be performed during a scan of a patient lying prone on their stomach on a scanner table 205 having an opening that provides access to the volume of tissue of the patient. The table, which may be made of a durable, flexible material such as sailcloth, may contour to the patient's body, thereby increasing scanning access to the axilla regions of the breast and increasing patient comfort. The opening in the table may allow the breast (or other appendage) to protrude through the table and be submerged in an imaging tank filled with water or another suitable fluid as an acoustic coupling medium that propagates acoustic waves.

Figure 2B:
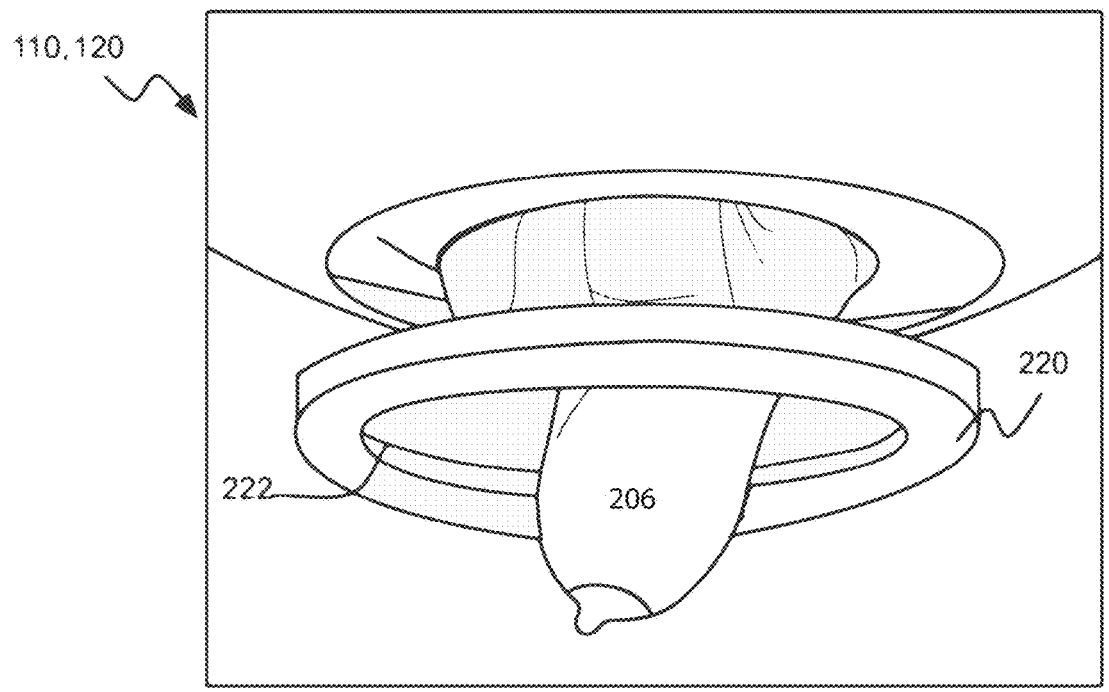
FIG. 2B is a schematic of a patient breast in an exemplary ultrasound scanner, in accordance with embodiments.
Figure 2C:
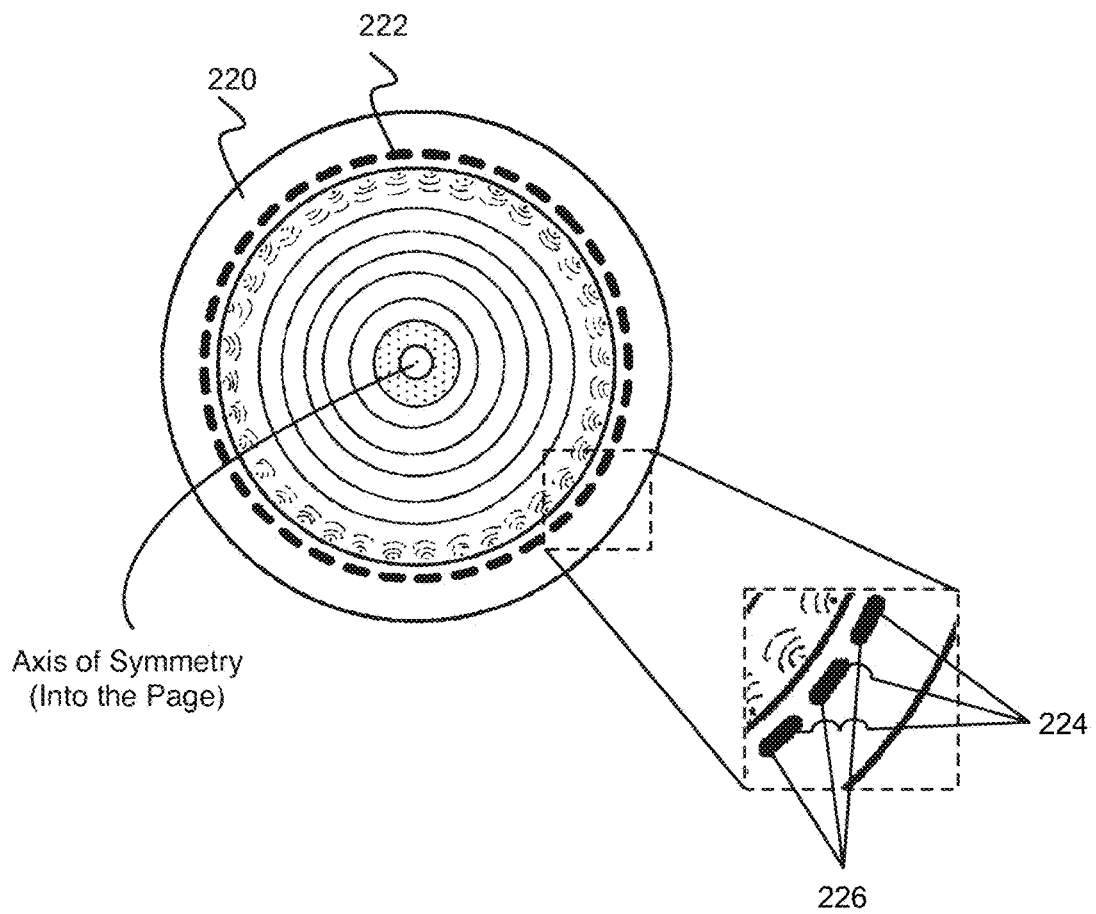
FIG. 2C is a schematic of an exemplary ultrasound transducer of an ultrasound scanner, in accordance with embodiments.

FIGS. 2B and 2C show a schematic of a patient breast in an exemplary ultrasound scanner and a schematic of an exemplary ultrasound transducer of an ultrasound scanner, in accordance with embodiments. FIGS. 2B and 2C show a ring-shaped transducer 220 with transducer elements 222. Transducer 220 may be located within the imaging tank and encircle or otherwise surround the volume of tissue 206. The transducer elements 222 may comprise an array of ultrasound transmitters 224 and/or an array of ultrasound receivers 226. Multiple ultrasound transmitters that direct safe, non-ionizing ultrasound pulses toward the tissue and multiple ultrasound receivers 226 that receive and record acoustic signals scattering from the tissue and/or transmitted through the tissue, may be distributed around the ring transducer 220. The transducer elements may comprise those configured to receive or transmit higher frequency acoustic waveforms and those configured to receive or transmit lower frequency acoustic waveforms. In an exemplary configuration, the ring transducer may be organized such that each ultrasound transmitter element may be paired with a corresponding ultrasound receiver element, each ultrasound transmitter element may be surrounded by two adjacent ultrasound transmitter elements, each ultrasound receiver element may be surrounded by two adjacent ultrasound receiver elements, and the transducer may be axially symmetric, as in FIG. 2C. In another configuration, the ultrasound transducer may comprise transducer units wherein each unit may be configured both to transmit and to receive.

During the scan, the ring transducer 220 may move to image all of the targeted tissue, such as in an anterior-posterior direction between the chest wall and the nipple region of the breast to acquire an acoustic data set including measurements such as acoustic reflection, acoustic attenuation, and sound speed. These data may be acquired at discrete scanning steps, or coronal "slices". The ring transducer 220 may be configured to scan step-wise in increments and/or travel continuously from the chest wall towards the nipple, and/or from the nipple towards the chest wall. However, the ring transducer 220 may additionally and/or alternatively receive data regarding any suitable biomechanical property of the tissue during the scan, and in any suitable direction.

In some embodiments, the scanner table may comprise an embodiment, variation, or example of the patient interface system described in the references incorporated herein and additionally or alternatively in U.S. application Ser. No. 14/208,181, entitled "Patient Interface System", U.S. application Ser. No. 14/811,316 entitled "System for Providing Scanning Medium", or P.C.T. International Pat. App. Pub. No. WO2017139389 entitled "System for Shaping and Positioning a Tissue Body", which are each hereby incorporated by reference in their entirety. However, steps 110 and/or 120 may additionally or alternatively be implemented using any other suitable patient interface system.

Emitting and detecting in step 110 may be performed in a rapid manner, such as with a data acquisition time of less than approximately 1 second per "slice", which may help to avoid motion artifacts in the subsequent morphology renderings and enables the use of contrast agents. However, any other suitable acquisition time may characterize emitting acoustic waveforms and/or detecting acoustic signals as in step 110. The emitted waveforms and/or detected signals may additionally or alternatively be beamformed on a transducing element.

A step 110 of the method 100 may comprise transmitting the plurality of acoustic signals from a transducer 220 to a computer 210 comprising one or more processors, computer readable media, and a display visible to a user 290 and additionally or alternatively comprising transmitting instructions to be received by a computer at a step 120. In other embodiments, steps 110 and/or 120 of the method 100 may additionally or alternatively comprise sending and/or retrieving acoustic signals from a computer readable storage medium such as a hard drive or an online server. Furthermore, in relation to detecting acoustic signals, the method 100 may additionally or alternatively comprise processing the set of acoustic signals according to at least one conditioning algorithm. For instance, for a given transmitter/detector pair of transducers, processing the set of acoustic signals may comprise one or more of: reading and correcting the raw data (detected acoustic signals) for DC variation; implementing a trapezoidal filter to bandpass useful frequencies and cut noise; and implementing any other suitable filter (high pass, low pass, etc.) to filter desired frequencies. Further signal processing may additionally or alternatively comprise discarding unusable signal such as "muting" in which recorded signal before the transmission wavefront and/or and after the longest applicable receiving time (e.g., "top muting" or "bottom muting"), further noise reduction processes, and other suitable signal processing steps. However, any other suitable conditioning process may additionally or alternatively be used.

Processing of Acoustic Data

At a step 120 of the method 100, a plurality of acoustic signals derived from acoustic waveforms transmitted through the volume of tissue may be received by a computer from a transducer. The acoustic signals may be processed by a computer as acoustic data. Acoustic data may be used to generate one or more "stacks" of 2D images corresponding to a series of "slices" of the volume of tissue for each measured acoustomechanical parameter. Each stack of 2D image data may comprise acoustic data associated with a particular parameter or property of the tissue, for example, any type of acoustic data such as acoustic reflection, acoustic sound speed, and acoustic attenuation. The processor 210 may additionally or alternatively generate a three-dimensional volumetric rendering based on the stack of two-dimensional images, and/or generate a three-dimensional volumetric rendering directly based on the received acoustic data. An image representation of any portion of the volume of tissue may depict any one or more acoustomechanical properties of the volume of tissue. For example, an image representation may depict acoustic attenuation, acoustic reflection, acoustic speed, and/or any suitable property of the tissue.

In one embodiment, a slice may correspond to regions of a volume of tissue scanned in an anterior to posterior manner (e.g., in coronal slices); however, the slices may correspond to slices in any other direction (e.g., at any angle relative to the anterior-posterior direction, in an inferior-superior direction, at any angle relative to the inferior-superior direction, in a medial-lateral direction, at any angle relative to the medial-lateral direction, etc.). Each acoustic data point within an acoustic slice may be associated with a particular value on a grid, including a position along the sliced axis, such that slices and the data may be ordered relative to each other to image the volume of tissue.

Figure 3:
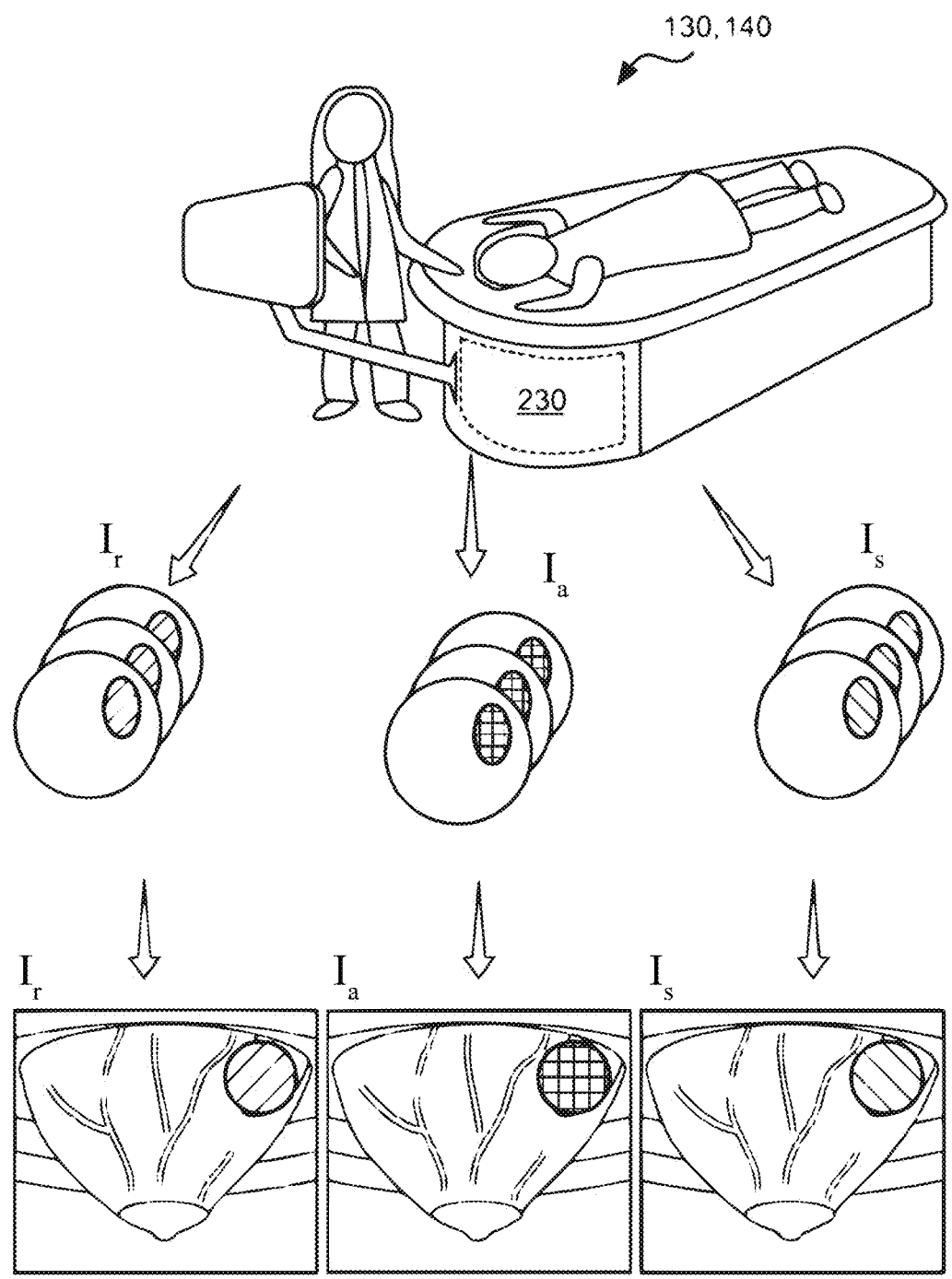
FIG. 3 is a schematic showing the generation of 3D renderings from stacks of 2D images of three acoustic data types, in accordance with embodiments.

FIG. 3 shows a schematic showing the generation of 3D renderings from stacks of 2D images of three acoustic data types, in accordance with embodiments. FIG. 3 shows a processor, a display, an imaging tank 230, and a scanner table of FIG. 2A. A set of acoustic reflection data, $I_r$, a set of acoustic speed data, $I_s$, and a set of attenuation data, $I_a$, corresponding to stacks of slices of the volume of tissue may each be collected. Additionally, FIG. 3 shows a 3D rendering of a volume of tissue corresponding to each data type. In another embodiment, generating a 3D acoustic rendering may comprise converting a 3D acoustic data set obtained by scanning in a 3D manner, directly to a 3D rendering.

The 3D renderings of any type of acoustic data may be combined or merged in whole or in part. In one embodiment, a merged rendering may comprise combining 3D renderings of at least two types of image data. In another embodiment, a merged rendering may comprise combining at least a portion of the set of 2D images from at least two types of image data. Any suitable formula or algorithm may be used to merge or fuse the various renderings into a single rendering.

Acoustic data may be rendered, for example, using methods described in U.S. Pat. Nos. 8,663,113; 9,113,835; and U.S. patent application Ser. No. 13/756,851; U.S. patent application Ser. No. 13/756,864; U.S. patent application Ser. No. 14/015,459; U.S. patent application Ser. No. 14/703,746; U.S. patent application Ser. No. 14/817,470; U.S. patent application Ser. No. 14/819,091; and P.C.T. International Pat. App. Pub. No. WO2017040866, which are each incorporated herein in their entirety by reference. At a step 130 of the method 100, a first reflection rendering that characterizes sound reflection may be generated from the plurality of acoustic signals, the first reflection rendering comprising a first distribution of reflection values across a region of the volume of tissue. A step 130 may be performed using a processor 210 included with or coupled to an ultrasound tomography scanner 200 of steps 110. Additionally or alternatively, step 130 may be performed on any suitable processor. Step 130 may generate a reflection rendering based on the set of acoustic signals from steps 110 and 120. Additionally or alternatively, a reflection rendering may be generated based on a set of acoustic signals from any suitable data. The reflection rendering may utilize envelope detected reflection data (ERF), raw radiofrequency reflection signals (e.g., REF image data, "radiofrequency", or RF data), which can be converted to a flash B-mode ultrasound image, and/or any suitable ultrasound image. The distribution of acoustic reflection signals may characterize a relationship (e.g., a sum, a difference, a ratio, etc.) between the reflected intensity and the emitted intensity of an acoustic waveform, a change in the acoustic impedance of a volume of tissue, and/or any other suitable acoustic reflection parameter.

A stack of 2D acoustic reflection images may be derived from changes in acoustic impedance of the tissue and may provide echo-texture data and anatomical detail for the tissue. Generating an acoustic reflection rendering may additionally and/or alternatively comprise generating a three-dimensional (3D) acoustic reflection rendering that may be a volumetric representation of the acoustic reflectivity of the volume of tissue. The reflection rendering can characterize a volume of tissue with a distribution of one or more of: fat tissue (e.g., fatty parenchyma, parenchymal fat, subcutaneous fat, etc.), parenchymal tissue, cancerous tissue, abnormal tissue (e.g., fibrocystic tissue, fibroadenomas, etc.), and any other suitable tissue type within the volume of tissue.

In some embodiments, the acoustic reflection rendering may be generated from a distribution of acoustic reflection signals received from an array of transducer elements transmitting and receiving at a frequency greater than the frequency of the array of transducer elements used to generate a rendering from another acoustic data type including, for example, the sound speed rendering or the attenuation rendering. In other embodiments, the acoustic reflection rendering may be generated from a distribution of acoustic reflection signals received from an array of transducer elements transmitting and receiving at a frequency less than the frequency of the array of transducer elements used to generate a rendering from another acoustic data type including, for example, the sound speed rendering or the attenuation rendering. The low frequencies (~1 MHz) may provide information on specular reflections (down to ~1 mm); however, imaging at higher frequencies (~1 to 5 MHz) may be better able to image the sub-mm granularity that provides information on speckle patterns. Therefore, it may be beneficial to generate a particular acoustic rendering at a particular frequency.

In some embodiments, the pulse echo contribution to the first reflection image of step 130 of a method 100 may be generated by the following method, as summarized below:
a. Specify path and read in REF image.
b. Remove all negative values from the REF image, such that $R_f = REF|_{>0}$
c. Perform variance normalization of the RF images.
d. Mitigate effect of outliers on pixel intensity distribution.
e. Smooth image.
f. Calculate the logarithm.
g. Remove outliers.
h. Normalize image values.
i. Remove ring feature (edge of transducer).

The method may comprise calculation of a number of mathematical relations including but not limited to, for example, averaging, truncation, normalization, smoothing, calculating the logarithm, addition, subtraction, multiplication, division, and any other simple mathematical relation that is known to one of ordinary skill in the art. The method may comprise smoothing the image data. The image may be smoothed by one or more algorithms such as but not limited to, for example, convolution with another function (such as a Gaussian or a Lorentzian), adjacent averaging, Fourier filtering, and any other algorithm suitable to smooth an image of a volume of tissue.

While a method for processing the first reflection image is shown above, in accordance with some embodiments, a person of ordinary skill in the art will recognize many adaptations and variations. Further, one or more steps shown above may be deleted or repeated, additional steps can be added, and the steps can be performed in any order.

At a step 140 of the method 100, a sound speed rendering that characterizes sound speed may be generated from the plurality of acoustic signals. The sound speed rendering may comprise a distribution of sound speed values across the region of the volume of tissue. A step 140 may be performed using a processor 210 included with or coupled to an ultrasound tomography scanner 200 of step 110. Additionally or alternatively, step 140 may be performed on any suitable processor. Step 140 may generate a sound speed rendering based on the set of acoustic signals from steps 110 and 120. Additionally or alternatively, a sound speed rendering may be generated based on a set of acoustic signals from any suitable data. The sound speed map may be generated based on a processing of sound transmission signals that pass through the volume of tissue in addition to backscattered signals from the volume of tissue. The sound speed map may characterize a part of the complex valued ultrasound impedance of the volume of tissue, the rate of travel of a waveform through the volume of tissue, a ratio of distance of travel through the volume of tissue over time between transmission and detection, or any other suitable acoustic speed parameter.

A stack of 2D acoustic sound speed images may be derived from the complex-valued impedance of the tissue and may provide anatomical detail of the tissue, wherein the impedance comprises a real portion corresponding to a phase velocity, and an imaginary portion corresponding to a sound attenuation. Generating an acoustic sound speed rendering may additionally and/or alternatively comprise generating a three-dimensional (3D) acoustic sound speed rendering that may be a volumetric representation of the acoustic sound speed of the volume of tissue. The sound speed rendering can characterize a volume of tissue with a distribution of one or more of: fat tissue (e.g., fatty parenchyma, parenchymal fat, subcutaneous fat, etc.), parenchymal tissue, cancerous tissue, abnormal tissue (e.g., fibrocystic tissue, fibroadenomas, etc.), and any other suitable tissue type within the volume of tissue.

Additionally or alternatively, the sound speed rendering may be generated from a waveform sound speed method. Such a method may comprise generating an initial sound speed rendering based on a time travel tomography algorithm. Additionally or alternatively, the initial sound speed rendering may be iteratively optimized until ray artifacts may be reduced to a pre-determined threshold for each of a plurality of sound frequency components. Such a method may comprise the method described in U.S. application Ser. No. 14/817,470, which is incorporated herein in its entirety by reference.

At a step 150 of the method 100, a second reflection rendering that characterizes sound reflection may be generated from the sound speed rendering, the second reflection rendering comprising a second distribution of reflection values across the region of the volume of tissue. A step 150 may be performed using a processor 210 included with or coupled to an ultrasound tomography scanner 200 of steps 110. Additionally or alternatively, step 150 may be performed on any suitable processor. Step 150 may generate a sound speed rendering based on the set of acoustic signals from steps 110 and 120. At a step 150, a second sound reflection rendering may be calculated from a sound speed rendering using a relation that involves a gradient with respect to position of the sound speed pixel or voxel. The distribution of acoustic reflection signals may characterize a relationship (e.g., a sum, a difference, a ratio, etc.) between the reflected intensity and the emitted intensity of an acoustic waveform, a change in the acoustic impedance of a volume of tissue, and/or any other suitable acoustic reflection parameter.

A stack of 2D acoustic reflection images may be derived from changes in acoustic impedance of the tissue and may provide echo-texture data and anatomical detail for the tissue. Generating an acoustic reflection rendering may additionally and/or alternatively comprise generating a three-dimensional (3D) acoustic reflection rendering that may be a volumetric representation of the acoustic reflectivity of the volume of tissue. The reflection rendering can characterize a volume of tissue with a distribution of one or more of: fat tissue (e.g., fatty parenchyma, parenchymal fat, subcutaneous fat, etc.), parenchymal tissue, cancerous tissue, abnormal tissue (e.g., fibrocystic tissue, fibroadenomas, etc.), and any other suitable tissue type within the volume of tissue.

The acoustic impedance (z) may be defined as $z=\rho c$ where, $\rho$ is the density and c is the speed of sound. Reflections occur when there are spatial gradients (e.g., changes) in the acoustic impedance. Such a gradient can be mathematically defined as the rate of change of the acoustic impedance, z, with respect to position $r=r(x,y)$:

$$\frac{\partial z}{\partial r} = \frac{\partial \rho}{\partial r}c + \frac{\partial c}{\partial r}\rho$$

Variations in density as well as speed of sound contribute to the gradient; however, waveform algorithms do not solve for density independently of speed of sound. The waveform algorithms make the simplifying assumption that ρ=constant. Consistent with this assumption, the waveform contribution to reflection imaging may be defined as:

$$R_w = \frac{\partial z}{\partial r} = \frac{\partial c}{\partial r}\rho = \text{constant} \cdot \frac{\partial c}{\partial r}$$

Thus, $R_w$ is assumed to be linearly proportional to the gradient of the sound speed image. This contribution provides a margin definition and texture contrast. Alternatively, the waveform algorithm may solve for both ρ and c so that the full form of the gradient can be calculated.

In some embodiments, the acoustic reflection rendering may be generated from a distribution of acoustic sound speed signals received from an array of transducer elements transmitting and receiving at a frequency greater than the frequency of the array of transducer elements used to generate a rendering from another acoustic data type including, for example, the first reflection speed rendering or an attenuation rendering. In other embodiments, the acoustic reflection rendering may be generated from a distribution of acoustic reflection signals received from an array of transducer elements transmitting and receiving at a frequency less than the frequency of the array of transducer elements used to generate a rendering from another acoustic data type including, for example, the sound speed rendering or the attenuation rendering. The low frequencies (~1 MHz) may provide information on specular reflections (down to ~1 mm); however, imaging at higher frequencies (~1 to 5 MHz) may be better able to image the sub-mm granularity that provides information on speckle patterns. Therefore, it may be beneficial to generate a particular acoustic rendering at a particular frequency.

In some embodiments, the second reflection image may be generated by the following method, as summarized below:
 a. Read in waveform sound speed image and make it the same size as the first reflection image
 b. Define a region that does not include the ring and calculate a gradient, $R_w = |\nabla c|$
 c. Eliminate outliers.
 d. Smooth image.
 e. Calculate the logarithm.
 f. Normalize the image values.

The method provides the calculation of a gradient. The gradient may comprise one or more algorithms such as image processing algorithms that may be used to "find edges" in an image. Such edge finding algorithms may include but are not limited to Sobel-Feldman operator, the Scharr operator, the Prewitt operator, and the Roberts Cross operator, and any other suitable method for finding edges in an image. In some embodiments, the gradient may be calculated using a Sobel-Feldman edge detector to highlight sharp changes in intensity in the selected image. A plurality of convolution kernels may be used to generate vertical and horizontal derivatives. The final image may be produced by combining the horizontal and vertical derivatives.

The method provides calculation of a number of mathematical relations including but not limited to, for example, averaging, truncation, normalization, smoothing, calculating the logarithm, addition, subtraction, multiplication, division, and any other simple mathematical relation that is known to one of ordinary skill in the art. The method provides smoothing the image data. The image may be smoothed by one or more algorithms such as but not limited to, for example, convolution with another function (such as a Gaussian or a Lorentzian), adjacent averaging, Fourier filtering, and any other algorithm suitable to smooth an image of a volume of tissue.

While a method for processing the waveform sound speed image is shown above, in accordance with some embodiments, a person of ordinary skill in the art will recognize many adaptations and variations. Further, one or more steps shown above may be deleted or repeated, additional steps can be added, and the steps can be performed in any order.

The reflection renderings of step 130 and step 150 of the method 100 may each be generated from acoustic data received from transducers which emit, detect, and/or may be sensitive to different frequencies. The first reflection rendering of step 130 may be generated from acoustic data received from a higher frequency (e.g., radiofrequency) sensitive transducer. A higher frequency transducer may increase the resolution of the acoustic data, allowing for smaller (e.g., less than 1 mm) features to be resolved; however, the transmission of higher frequency sound may be decrease with increased frequency. The second reflection rendering of step 150 may be generated from acoustic data received from a lower frequency transducer. A lower frequency may allow for greater ultrasound penetration, increasing the contrast between lower sound speed and higher sound speed regions of the volume of tissue. The second reflection rendering from the lower frequency transducer may also show greater contrast between regions of high and low reflectivity.

At a step 160 of the method 100, one or more combined images may be rendered based on the first reflection rendering and the second reflection rendering, thereby generating the enhanced image of the volume of tissue. The two images may be combined by a relation that includes: an element wise average or a weighted average, an element wise sum or a weighted sum, an element wise product or a weighted product, a convolution of the two images, or any other mathematical relationship sufficient to render a combined image. This relation may additionally include other steps including, for example, averaging, truncation, renormalization, smoothing (such as by convolution with another function, adjacent averaging, Fourier filtering, etc.), addition, subtraction, multiplication, division, or any other appropriate mathematical relation appropriate to render a combined image.

In some embodiments, the first and the second reflection renderings, $R_f$ and $R_w$, may be combined by the following method, as summarized below:
 a. Reduce weight of $R_w$
 b. Add the two components While a method for combining two reflection images is shown above, in accordance with some embodiments, a person of ordinary skill in the art will recognize many adaptations and variations. Further, one or more steps shown above may be deleted or repeated, additional steps can be added, and the steps can be performed in any order.

Figure 4:
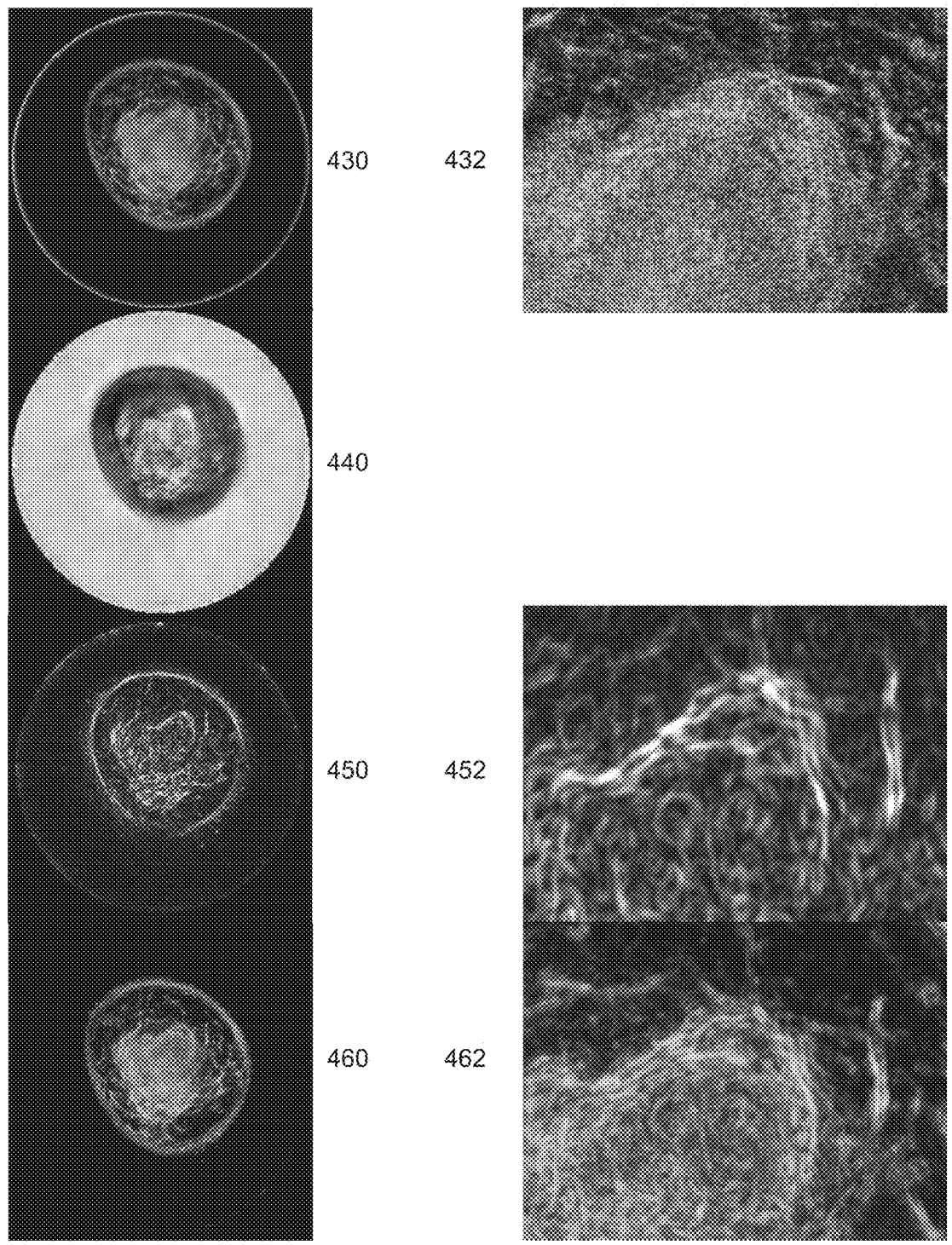
FIG. 4 shows exemplary coronal slices of several three dimensional renderings of each of several acoustic data types of the same patient breast comprising a cancerous lesion at various steps in a method of generating an enhanced image, in accordance with embodiments.

FIG. 4 shows exemplary coronal slices of several three dimensional renderings of each of several acoustic data types of the same patient breast comprising a cancerous lesion at various steps in a method 100 of generating an enhanced image, in accordance with embodiments. Slice 430 shows an exemplary RF reflection image, and slice 432 shows a magnified image of a lesion in a volume of tissue in slice 430. Step 130 of a method 100 may comprise generation of such a RF reflection image as 430 or 432. Slice 440 shows an exemplary waveform sound speed image generated from the method described the reference incorporated above. Step 140 of a method 100 may comprise generation of such a waveform sound speed image as 440. Slice 450 shows an exemplary second reflection rendering, and slice 452 shows a magnified image of a lesion in a volume of tissue in slice 450. Step 150 of a method 100 may comprise generation of such a second reflection rendering as 450 or 452. Slice 460 shows an exemplary enhanced reflection image, and slice 462 shows a magnified image of a lesion in a volume of tissue in slice 460. Step 160 of a method 100 may comprise generation of such an enhanced reflection image as 460 or 462.

Magnified images 432, 452, and 462 may correspond to images at steps 130, 150, and 160 of the method 100, respectively. Images 432, 452 and 462 show increasing improvement in contrast, resolution, and conspicuity of spiculations around a lesion.

For example, an enhancement in resolution may comprise an increase in resolution of the image from an initial resolution of greater than about 1 mm, greater than about 2 mm, greater than about 3 mm, greater than about 4 mm, greater than about 5 mm, greater than about 6 mm, greater than about 7 mm, greater than about 8 mm, greater than about 9 mm, or greater than about 10 mm; to an enhanced resolution of less than about 1.0 mm, less than about 0.9 mm, less than about 0.8 mm, less than about 0.7 mm, less than about 0.6 mm, less than about 0.5 mm, less than about 0.4 mm, less than about 0.3 mm, less than about 0.2 mm, or less than about 0.1 mm. For example, an enhancement in contrast may comprise an increase in contrast of the image by a factor of at least about 2, at least about 3, at least about 4, at least about 5, at least about 6, at least about 7, at least about 8, at least about 9, or at least about 10. For example, an enhancement may comprise an increase in conspicuity of lesions in the volume of tissue by a factor of at least about 2, at least about 3, at least about 4, at least about 5, at least about 6, at least about 7, at least about 8, at least about 9, or at least about 10. For example, an enhancement may comprise an increase in specificity of lesion characterization in the volume of tissue such that the specificity is at least about 75%, at least about 80%, at least about 85%, at least about 90%, or at least about 95%. In some embodiments, the tissue comprises breast tissue.

Since cancerous lesions may show more frequent spiculations, the combined image 462 may improve the classification of cancerous masses from fibroadenomas, or other benign masses. The combined reflection image may improve the conspicuity of the boundary around a lesion. For example, an enhancement may comprise an increase in conspicuity of lesions in the volume of tissue by a factor of at least about 2, at least about 3, at least about 4, at least about 5, at least about 6, at least about 7, at least about 8, at least about 9, or at least about 10. Since cancerous lesions may show irregular boundaries, the combined image may improve the classification of cancerous masses from fibroadenomas, which may have smoother and more regular boundaries. As shown in FIG. 4, as the method progresses, the reflection images show increased contrast and resolution. Additionally, the edge of the cancerous lesion and the spiculations in the volume of breast in FIG. 4 become significantly more conspicuous.

In other embodiments, the method of generating an enhanced image of a volume of tissue may additionally comprise correction of the enhanced reflection image for contributions from fat tissue. Some frequencies used to create reflection images of fatty tissues can be relatively anechoic. This can be less than ideal for the reviewing radiologist because the fatty tissues may compete with lesions for conspicuity. In some embodiments, the method provides a method to artificially boost regions of fat in brightness to levels comparable to the other hyperechoic structures in the breast. In some embodiments the method relies upon independent knowledge of the distribution of fat in the breast obtained from the sound speed images. Using numerical thresholding fat may be differentiated from other tissue components of the breast by its low sound speed. The thresholding method may render the fatty tissue approximately the same echogenicity as the denser tissues, such that only lesions remain hypoechoic in the image stack.

Figure 5:
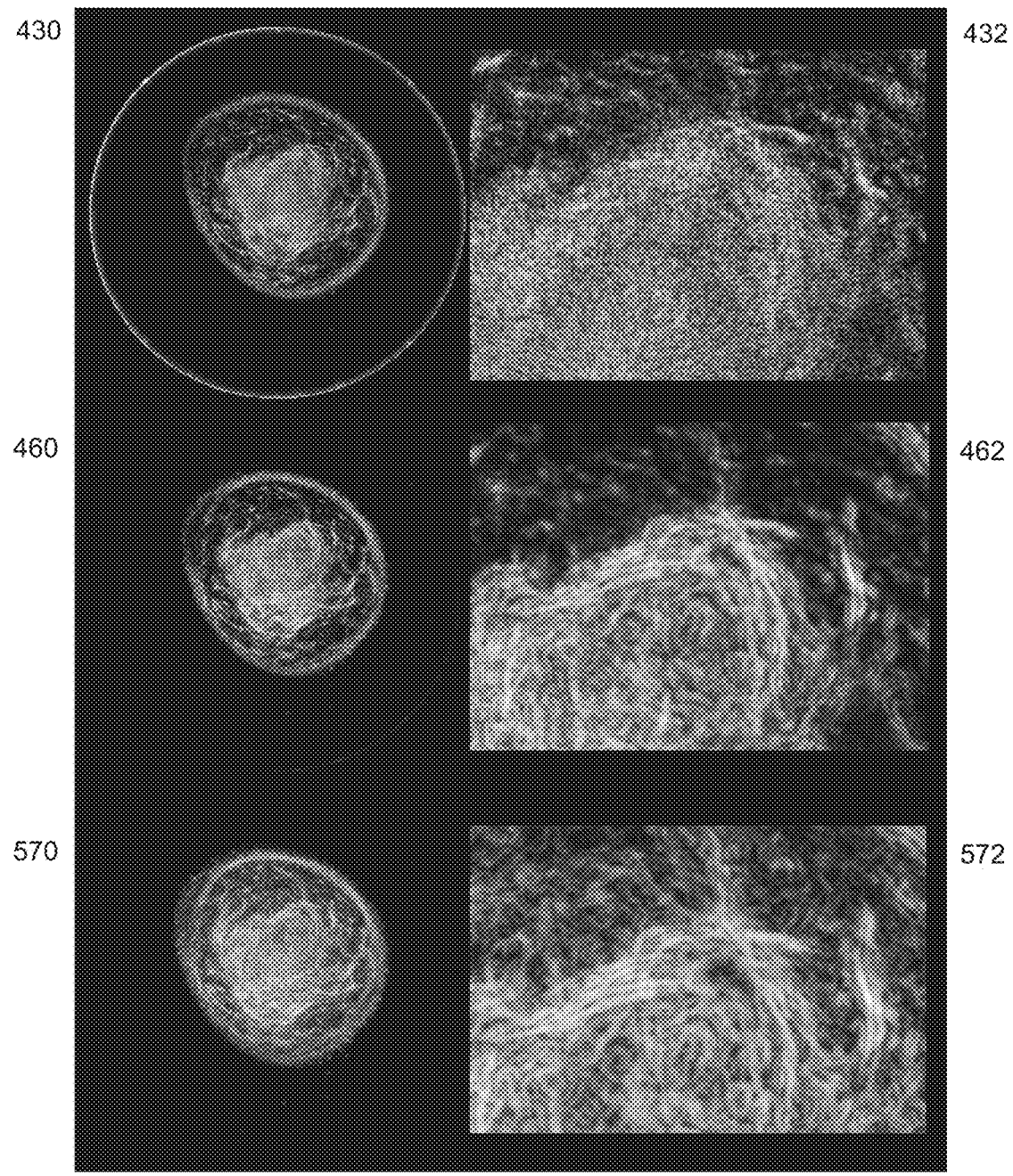
FIG. 5 shows exemplary coronal slices of the same patient breast from FIG. 4 additionally comprising an enhanced image after fat correction, in accordance with embodiments.

FIG. 5 shows exemplary coronal slices the same patient breast from FIG. 4 additionally comprising an enhanced image after fat correction, in accordance with embodiments. Slice 430 shows an exemplary RF reflection image, and slice 432 shows a magnified image of a lesion in a volume of tissue in slice 430. Slice 460 shows an exemplary enhanced reflection image, and slice 462 shows a magnified image of a lesion in a volume of tissue in slice 460. Slice 570 shows an exemplary enhanced reflection image after fat correction, and slice 572 shows a magnified image of a lesion in a volume of tissue in slice 570.

In some embodiments, the correction of the enhanced reflection image for contributions from fat may be implemented by the following method, as summarized below:
   a. Read in waveform sound speed image
   b. Define a threshold for fat sound speed and a threshold for dense tissue
   c. Normalize relative to the threshold for fat sound speed
   d. Define a transformation that yields a greater coefficient for c values below the threshold and unity for c values above the threshold
   e. Read in the enhanced reflection image
   f. Apply the transformation to the enhanced reflection image In some embodiments, the mathematical operation that defines the transformation may have the general form of a Gaussian function, such as one given by:

$$R_{corr} = R_{wafer} \cdot \left[1 + e^{-\frac{(c-c_f)^2}{\sigma^2}}\right],$$

where c=speed of sound from the sound speed image and $c_f$ is the speed of sound of fat. Thus, each pixel in the $R_{wafer}$ image may be modified by a value that depends on how far away the corresponding c may be from that of fat. Thus, for values of $c=c_f$, $R_{wafer}$ may be multiplied by 2, while for distant values of c ($c \gg c_f$), the multiplying factor may decline to 1 (e.g., no modification to pixel value). The scaling constant $\sigma$ may govern the contrast of the fat relative to denser tissues in the final $R_{corr}$ image.

In other embodiments, the mathematical operation that defines the transformation may have the form of a step function. In other embodiments, the mathematical operation may comprise any type function that may represent a probability distribution of a single random variable such as but not limited to, for example, a Lorentzian distribution; a Voigt distribution; a logistic distribution; a Laplace distribution; a Landau distribution; a Student's t distribution; an error function; a Dirac delta function; and a Weibull distribution.

While a method for processing the waveform sound speed image is shown above, in accordance with some embodiments, a person of ordinary skill in the art will recognize many adaptations and variations. Further, one or more steps shown above may be deleted or repeated, additional steps can be added, and the steps can be performed in any order.

In other embodiments, the method of generating an enhanced image of a volume of tissue may additionally comprise classifying, based on the one or more combined images, different types of lesions in the volume of tissue as at least one of a cancerous tumor, a fibroadenoma, a cyst, a nonspecific benign mass, and an unidentifiable mass. The method of classifying may comprise the method of characterizing a volume of breast tissue based on plurality of prognostic parameters interior and exterior to a region of interest described herein, which method may improve the specificity of lesion characterization by up to 10%, for example, within a range defined between any two of the following values: about 0.1%, about 1%, about 5%, and about 10%. Additionally or alternatively, classifying a lesion may be performed based on qualitative observations by skilled user, according to an existing classification method, such as Breast Imaging Reporting and Data System (BI-RADS). Additionally or alternatively, classifying a lesion may be performed based on any accepted classification method using a reflection image.

Figure 6A:
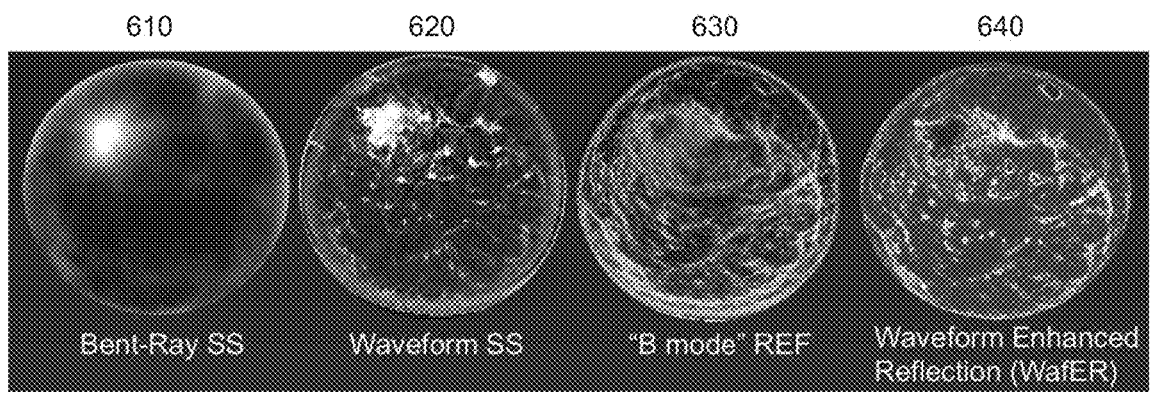
FIG. 6A shows exemplary coronal slices the same patient breast comprising a cancerous lesion and a malignant node from different types of acoustic renderings, in accordance with embodiments.
Figure 6B:
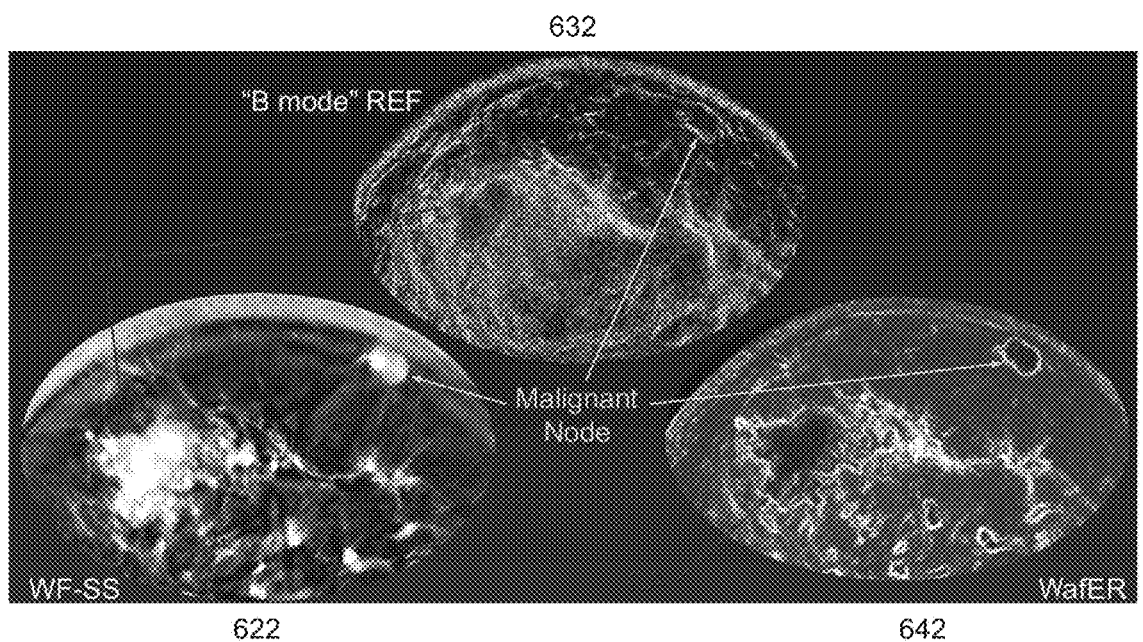
FIG. 6B shows magnified images of the acoustic renderings in FIG. 6A, in accordance with embodiments.

FIG. 6A shows exemplary coronal slices of the same patient breast comprising a cancerous lesion and a malignant node from different types of acoustic renderings, in accordance with embodiments. FIG. 6A shows how the method of generating an enhanced reflection image described herein may aid in classification of a lesion. Slice 610 is a "Bent-Ray" sound speed image; slice 620 is a "waveform" sound speed image; slice 630 is a "B-mode" reflection image; and slice 640 is an enhanced reflection image based on the methods disclosed herein. FIG. 6B shows magnified images 622, 632, and 642 of the acoustic rendering in 620, 620 and 640, respectively, in accordance with embodiments. Images 610 and 620 highlight the improvement in resolution of waveform based sound speed images, such as image 620, over time of flight sound speed images, such as image 610. In the magnified images, the enhanced reflection image 642 shows more conspicuous edges around the cancer (CA) and the malignant node, more conspicuous spiculations around the cancer, and increased image contrast over the "B mode" reflection image.

Margin Boundary Selection

Figure 7:
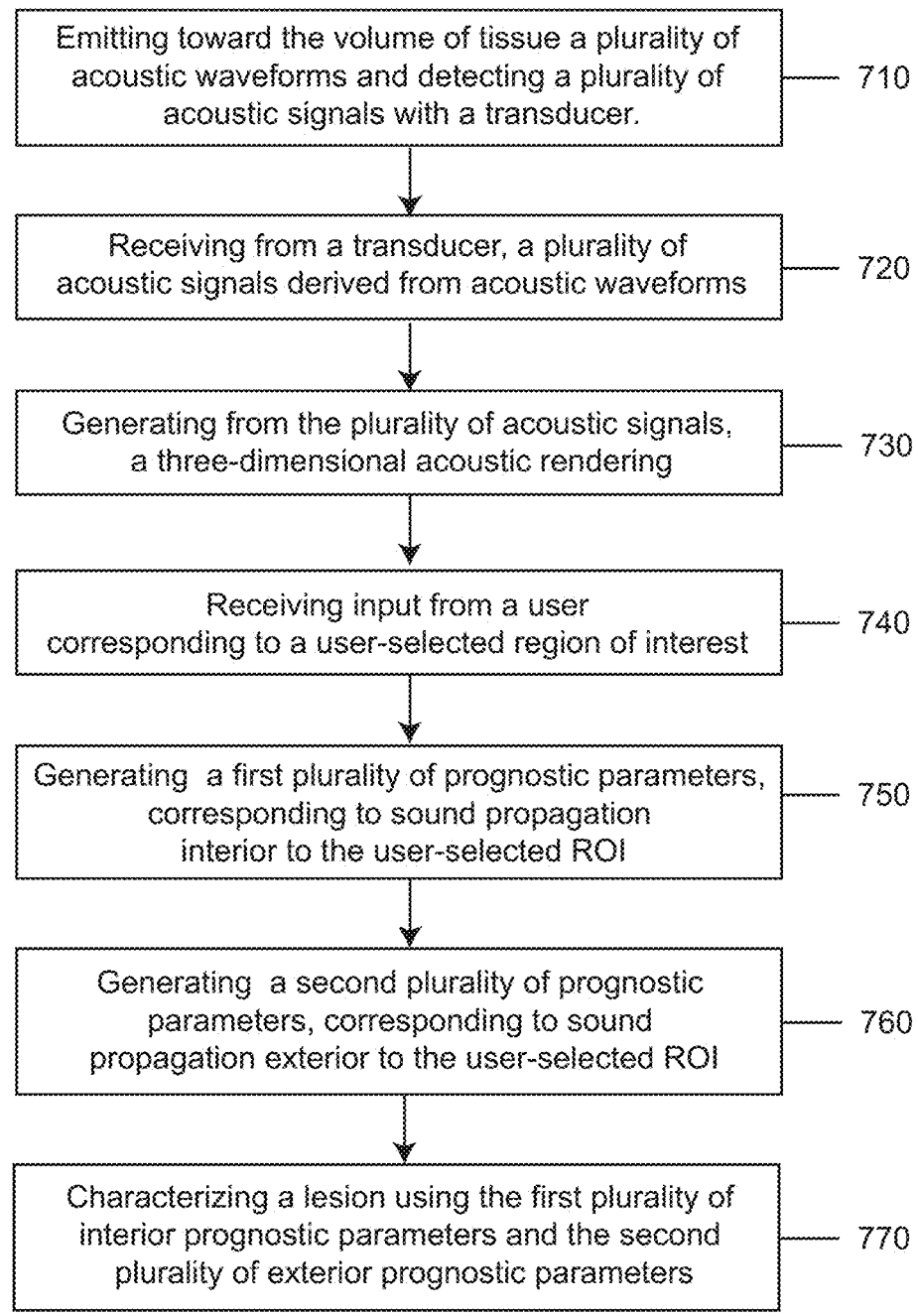
FIG. 7 shows an exemplary method for characterizing a volume of breast tissue of a patient, in accordance with embodiments.

Embodiments of the present disclosure provide a method for characterizing a volume of breast tissue of a patient. The method may be implemented by a computer comprising one or more processors and computer readable media comprising instructions. FIG. 7 shows an exemplary method 700 for characterizing a volume of breast tissue of a patient, in accordance with some embodiments. A method 700 may comprise emitting toward the volume of tissue a plurality of acoustic waveforms and detecting from the volume of tissue a plurality of acoustic signals with a transducer, wherein the transducer may comprise an array of ultrasound transmitters and an array of ultrasound receivers configured to surround the volume of tissue 710. The method 700 may further comprise receiving from a transducer, a plurality of acoustic signals derived from acoustic waveforms transmitted through the volume of tissue 720. The method 700 may further comprise generating from the plurality of acoustic signals, a three-dimensional acoustic rendering that characterizes sound propagation within the volume of tissue 730. The method 700 may further comprise receiving input from a user corresponding to a user-selected region of interest 740. The method 700 may further comprise generating from the acoustic rendering a first plurality of prognostic parameters corresponding to sound propagation interior to the user-selected region of interest 750. The method 700 may further comprise generating from the acoustic rendering a second plurality of prognostic parameters corresponding to sound propagation exterior to the user-selected region of interest 760. The method 700 may further comprise characterizing a lesion within the volume of tissue using the first plurality of interior prognostic parameters and the second plurality of exterior prognostic parameters 770.

In some embodiments, method 700 may function to characterize a volume of tissue (e.g., a whole breast, another organ) according to a rendering of ultrasound images that enhance target objects within a field of view. Additionally or alternatively, the volume of tissue may comprise a distribution of one or more of: fat tissue (e.g., fatty parenchyma, parenchymal fat, subcutaneous fat, etc.), parenchymal tissue, cancerous tissue, abnormal tissue (e.g., fibrocystic tissue, fibroadenomas, etc.), and any other suitable tissue type within the volume of tissue. Method 700 may be used to characterize tissue of a human breast, but may additionally or alternatively be used to characterize tissue of an arm, leg, other appendage, and/or any suitable volume of tissue in a human or other animal. In relation to current ultrasound methods and systems, method 700 may improve specificity in characterization of types of masses by up to 10%, for example, within a range defined between any two of the following values: about 0.1%, about 1%, about 5%, and about 10%. Such masses may include but are not limited to: a cancerous tumor, a fibroadenoma, a cyst, a nonspecific benign mass, and an unidentifiable mass. Method 700 may, however, function to enable diagnosis, monitoring, and/or characterization of a volume of tissue in any other suitable manner.

In some embodiments, method 700 may be used to characterize the tissue to facilitate diagnoses of cancer, assess its type and determine its extent (e.g., to determine whether a mass in the tissue may be surgically removable), or to assess risk of cancer development (e.g., measuring breast tissue density). In yet another embodiment, method 700 may be used to characterize and/or investigate particular aspects of the tissue, such as to determine whether a mass in the tissue may be a tumor, cyst, fibroadenoma, or other kind of mass. Method 700 may be used in any suitable application for imaging a volume of tissue or other suitable object. Method 700 may be implemented, at least in part, by way of an embodiment, variation, and/or example of the system 200 described in the section titled "Ultrasound Tomography System" below; however, method 700 may additionally or alternatively be implemented using any other suitable system.

While FIG. 7 shows a method of generating an enhanced image of a volume of tissue, in accordance with embodiments, a person of ordinary skill in the art will recognize many adaptations and variations. Further, one or more steps shown in FIG. 7 may be deleted or repeated, additional steps can be added, and the steps can be performed in any order.

At a step 710 of the method 700, a plurality of acoustic waveforms may be emitted toward the volume of tissue and a plurality of acoustic signals may be detected from the volume of tissue with a transducer. The transducer may comprise an array of ultrasound transmitters and an array of ultrasound receivers configured to surround the volume of tissue. At a step 720 of the method 700, a plurality of acoustic signals derived from acoustic waveforms transmitted through the volume of tissue may be received by a computer from a transducer. Steps 710 and 720 function to gather acoustic data from which renderings of the volume of tissue may be derived in other steps of the method 700. At step 710 of the method 700, emitting acoustic waveforms and detecting a set of acoustic signals may be performed with an ultrasound tomographic scanner 200, for example as described in the section titled "Ultrasound Tomography System", and using methods similar to those described in the incorporated references. However, any suitable ultrasound device or scanner may be used. Additionally or alternatively, a step 710 and a step 720 may be performed using the methods described in the section titled "Emitting and Receiving Acoustic signals".

At a step 730 of the method 700, a three-dimensional acoustic rendering that characterizes sound propagation within the volume of tissue may be generated from the plurality of acoustic signals. The acoustic signals may be processed by a computer as acoustic data. Acoustic data may be used to generate one or more "stacks" of 2D images corresponding to a series of "slices" of the volume of tissue for each measured acoustomechanical parameter. Each stack of 2D image data may comprise acoustic data associated with a particular parameter or property of the tissue, for example, any type of acoustic data such as acoustic reflection, acoustic sound speed, and acoustic attenuation. The processor 210 may additionally or alternatively generate a three-dimensional volumetric rendering based on the stack of two-dimensional images, and/or generate a three-dimensional volumetric rendering directly based on the received acoustic data. An image representation of any portion of the volume of tissue may depict any one or more acoustomechanical properties of the volume of tissue. For example, an image representation may depict acoustic attenuation, acoustic reflection, acoustic speed, and/or any suitable property of the tissue.

Additionally or alternatively, a step 730 may be performed using a method 100 for generating an enhanced image of a volume of tissue described herein. Additionally or alternatively, a step 730 may be performed using the methods described in the section titled "Processing of Acoustic Data" and in the methods in the references incorporated therein. Such methods may include generating a waveform sound speed rendering and generating a first reflection rendering.

In one embodiment, a slice may correspond to regions of a volume of tissue scanned in an anterior to posterior manner (e.g., in coronal slices); however, the slices may correspond to slices in any other direction (e.g., at any angle relative to the anterior-posterior direction, in an inferior-superior direction, at any angle relative to the inferior-superior direction, in a medial-lateral direction, at any angle relative to the medial-lateral direction, etc.). Each acoustic data point within an acoustic slice may be associated with a particular value on a grid, including a position along the sliced axis, such that slices and the data may be ordered relative to each other to image the volume of tissue.

Additionally or alternatively, generating a set of 2D acoustic attenuation images may be derived from the imaginary part of the acoustic impedance of the tissue and may yield anatomical detail for the tissue. Generating an acoustic attenuation rendering may additionally and/or alternatively comprise generating a three-dimensional (3D) acoustic attenuation rendering that may be a volumetric representation of the acoustic attenuation of the volume of tissue. The attenuation rendering can characterize a volume of tissue with a distribution of one or more of: fat tissue (e.g., fatty parenchyma, parenchymal fat, subcutaneous fat, etc.), parenchymal tissue, cancerous tissue, abnormal tissue (e.g., fibrocystic tissue, fibroadenomas, etc.), and any other suitable tissue type within the volume of tissue. Additionally or alternatively, generating an acoustic attenuation rendering may comprise a method described in the references incorporated herein.

The 3D renderings of any type of acoustic data may be combined or merged in whole or in part. In one embodiment, a merged rendering may comprise combining 3D renderings of at least two types of image data. In another embodiment, a merged rendering may comprise combining at least a portion of the set of 2D images from at least two types of image data. Any suitable formula or algorithm may be used to merge or fuse the various renderings into a single rendering.

At a step 740 of the method 700, input may be received from a user corresponding to a user-selected region of interest. A region of interest (ROI) may be identified by a user based on the 3D renderings of any form acoustic data including acoustic attenuation, acoustic sound speed, and acoustic reflection and additionally including combined or merged renderings. The ROI may correspond to a mass within for example a breast tissue. The mass may be for example, a cancerous mass, a benign fibroadenoma, a cyst, another benign finding, an unidentifiable mass (for example, there may be no finding), or any suitable characterization or classification. In one embodiment, the ROI may be selected by a user, for example, by tracing the ROI "free-hand" or drawing a simple shape such as a circle or ellipse.

Additionally or alternatively, the selection of an ROI may be aided or optimized by a computer-implemented algorithm, wherein the computer comprises a processor with instructions to implement the algorithm. The processor may aid or optimize selection of an ROI based on threshold values of any acoustic data type and/or multiples of data types including combinations of data types. The processor may aid or optimize selection of an ROI based on a known morphology, such as through the use of image recognition algorithms.

Figure 8A:
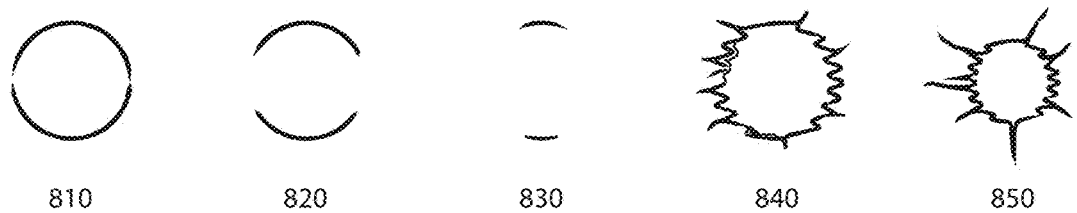
FIG. 8A shows exemplary regions of interest comprising various margin boundaries with varying boundary morphologies, in accordance with embodiments.

The ROI may comprise a margin boundary between the ROI and the surrounding tissue. FIG. 8A shows exemplary ROIs comprising various user-selected and/or computer selected margin boundaries and additionally comprising varying boundary morphologies, in accordance with embodiments. The margin boundary may be completely identified at the start of analysis; however, additionally or alternatively, the margin boundary may be incomplete at the start of analysis and optimized by a computer program. In FIG. 8A, the left three margin boundaries show various degrees of completeness at the start of analysis. The margin boundary 810 is greater than two-thirds complete; margin boundary 820 is between one-third and two-thirds complete; margin boundary 830 is less than ⅓ complete.

The margin boundary may also comprise a morphology which may be used in a classifier model. Such morphologies may comprise, for example, those with smooth edges, those with irregular and/or rough edges, for example, those which have one or a plurality of elongate elements or those which may be speculated, those which may be predominantly round or ellipsoid, or any other shape which a lesion in a tissue may reasonably take. Margin boundaries 840 and 850 are complete and show exemplary morphologies of the margin boundary. Margin boundary 840 shows an irregular margin boundary. Margin boundary 850 shows significant speculation, such as may indicate a cancerous lesion.

From a selected ROI with an identified margin boundary, one or a plurality of interior and exterior regions of interest may be identified. The interior region(s) of interest may comprise one or a plurality of layers starting at the margin boundary and continuing further inside the ROI. The exterior regions of interest may comprise one or a plurality of layers starting at the margin boundary and continuing further outside the ROI. The interior and exterior layers of the ROI may each comprise layers classified as "near" and "distant". The "near" layers may be classified as being close to the boundary. The "distant" layers may be classified as being far from the boundary. For example, the interior layers of the region of interest may comprise layers near the boundary and distant from the boundary. For example, the external layers of the region of interest may comprise layers near the boundary and distant from the boundary.

Figure 8B:
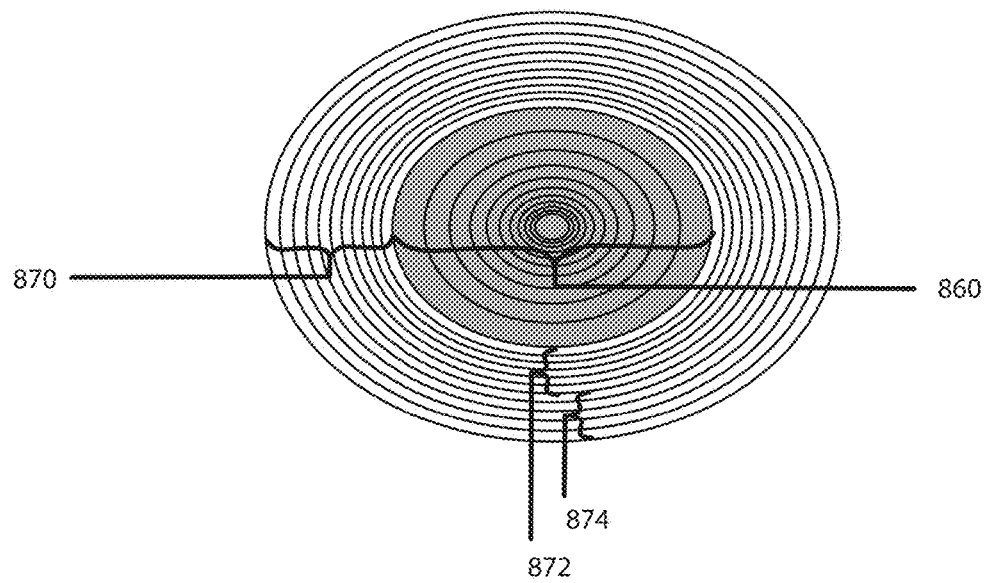
FIG. 8B shows an exemplary ellipsoidal region of interest with a margin boundary and internal and external layers, in accordance with embodiments.

FIG. 8B shows an exemplary ellipsoidal ROI 860 with a margin boundary and internal and external layers, in accordance with embodiments. The margin boundary may be selected by a user and additionally or alternatively selected by a user and optimized with the aid of a computer implemented algorithm. The exemplary ROI in FIG. 8B is ellipsoidal; however, an ROI may have any morphology that a lesion may take, some of which are listed with reference to FIG. 8A. Additionally or alternatively, the ROI in FIG. 8B may correspond to an initial ROI selected by a user to be optimized or assisted by a computer program. ROI 860 has an interior in grey and an exterior 870 in white. The exterior of the ROI may extend further than the lines drawn around the ROI in FIG. 8B.

In some embodiments, the interior of ROI 860 may be segmented into layers shown with solid lines drawn inside the grey area. FIG. 8B shows an interior of a region of interest which has been segmented into 10 layers; however, the interior of the ROI can be segmented into any number of layers. The layers maybe evenly spaced or may get smaller or larger from interior to exterior. Additionally or alternatively, the exterior of ROI 860 may be segmented into layers shown with solid lines drawn outside of ROI 860. FIG. 8B shows an exterior of a region of interest which has been segmented into 10 layers; however, the exterior of the ROI can be segmented into any number of layers. The layers maybe evenly spaced or may get smaller or larger from interior to exterior. The ROI can be segmented into layers before or after finalization of an ROI.

Additionally or alternatively, a set of layers interior or exterior to the region of interest may be classified as "near" or "distant". Exterior region 870 in FIG. 8B has five layers classified as "near" 872 and five layers classified as "distant" 874. The number of layers classified as near or distant may comprise any subset of layers interior or exterior to the region of interest. Additionally or alternatively, the layers may be divided evenly into near and distant or unevenly. Additionally or alternatively, the layers classified near and distant may overlap such that an individual layer may fall into both the near and distant classification. The layers may be classified as near or distant before or after finalization of the ROI.

Prognostic Parameters

The selected ROI may be characterized using a classifier model based on a set of prognostic parameters. Set of prognostic parameters may comprise one or many types of acoustic data corresponding to sound propagation in a volume of tissue. Such types of acoustic data includes but is not limited to, for example: quantitative acoustic data (e.g., acoustic sound speed, acoustic attenuation, and acoustic reflection), quantitative morphological data (e.g., an area, diameter, ellipticity, etc. of an ROI), and qualitative morphological data (e.g., a user assessed parameter). Additionally or alternatively, the classifier model may use threshold values of any prognostic parameter and/or multiples of prognostic parameters. A threshold value of a prognostic parameter may be selected from a known value inherent to a lesion type. A threshold value of a prognostic parameter may be selected by a user. A threshold value of a prognostic parameter may be selected based on a computer-implemented algorithm. A selected threshold value and/or combination of threshold values may be optimized by such an algorithm in order to improve characterization of a lesion.

At a step 750 of the method 700, a first plurality of prognostic parameters corresponding to sound propagation interior to the user-selected region of interest are generating from the acoustic rendering. At a step 760 of the method 700, a second plurality of prognostic parameters corresponding to sound propagation exterior to the user-selected region of interest may be generated from the acoustic rendering. Each layer, subset of layers, classification of layers, and/or ROI may have one or many associated quantitative prognostic parameters. Quantitative prognostic parameters may comprise, for example, a mean, a median, a mode, a standard deviation, and volume-averages thereof of any acoustic data type. A quantitative prognostic parameter may be calculated from a combination of data types. For example, a quantitative prognostic parameter may comprise a difference of prognostic parameters between a region in the interior of the ROI and in the exterior of the ROI. In another example, a quantitative prognostic parameter may comprise a difference between regions of interest, layers, classification of layers, etc. A quantitative prognostic parameter may comprise a ratio of a prognostic parameter with, for example, another prognostic parameter, a known biological property, etc. Additionally or alternatively, a quantitative prognostic parameter may be weighted by a spatial distribution. Additionally or alternatively, a quantitative prognostic parameter may be calculated from a volume average of an acoustic data type over, for example, a region of interest, a layer, a plurality of layers, a classification of layers, etc.

Each layer, classification of layers, and/or ROI may have one or many associated qualitative prognostic parameters. One or more qualitative prognostic parameters may be used in combination to generate other qualitative prognostic parameters. Qualitative prognostic parameters may comprise one or a combination of the shape, the sharpness, the architecture and/or other characteristics of the morphology renderings. The qualitative prognostic parameters may characterize any suitable aspect of the biomechanical property renderings. A qualitative prognostic parameter may be converted by a user or a computer into a semi-quantitative prognostic parameter, such as "1" for an indistinct margin and "2" for a sharp margin of the region of interest in the acoustic reflection rendering. As another example, a qualitative prognostic parameter may be converted by a user or a computer to a semi-quantitative parameter such as a value on an integer scale (e.g., 1 to 5) that classifies the degree to which the qualitative aspect is expressed. For instance, margin sharpness of the region of interest in the acoustic reflection rendering may be classified with a reflection index as "1" if it is very sharp, "3" if it is moderately indistinct, or "5" if it is very indistinct.

Qualitative, quantitative, and semi-quantitative prognostic parameters may be combined in order to generate other extended prognostic parameters. These extended prognostic parameters may comprise the existing Breast Imaging Reporting and Data System (BI-RADS), wherein a lesion is characterized on an integer scale from 1 to 5, but may also comprise other extended prognostic parameters comprising acoustic data. The prognostic parameters disclosed herein may be time dependent. The time dependence of one or a plurality of prognostic parameters may comprise a prognostic parameter. Although all of these quantitative and qualitative prognostic parameters may be determined, only a portion of these parameters may be determined.

Table 1 shows exemplary fields for organizing prognostic parameters by region of interest and by classification of region of interest, including fields for the mean (e.g., the volume-average) and standard deviation (e.g., the volume-standard-deviation) of a particular acoustic data types A, B, and C over a volume of tissue. The table also comprises prognostic parameters associated with differences between classifications of layers associated with a region of interest.

| Region | A B C |
|---|---|
| Tumor (T) | Mean |
|  | Std. Dev. |
| Peritumoral (P) | Mean |
|  | Std. Dev. |
| Near peritumoral (nP) | Mean |
|  | Std. Dev. |
| Distant peritumoral (dP) | Mean |
|  | Std. Dev. |
| Relative Peri (T-P) | Mean |
|  | Std. Dev |
| RelNearP (T-nP) | Mean |
|  | Std. Dev |
| Rel DistanP (T-dP) | Mean |
|  | Std. Dev |

The region "tumor" characterizes a set of prognostic parameters associated with acoustic data interior to a region of interest. The region "peritumoral" characterizes a set of prognostic parameters associated with acoustic data exterior to a region of interest. The region "near peritumoral" characterizes a set of prognostic parameters associated with a classification of layers which may be near to the margin boundary of the region of interest and may be exterior to the region of interest. The region "distant peritumoral" characterizes a set of prognostic parameters associated with a classification of layers which may be distant to the margin boundary of the region of interest and may be exterior to the region of interest. The region "Relative Peri" characterizes a set of prognostic parameters associated with the difference between a set of interior prognostic parameters less a set of exterior prognostic parameters. The region "RelNearP" characterizes a set of prognostic parameters associated with the difference between a set of interior prognostic parameters less a set of prognostic parameters which may be associated with a classification of layers, which may be near to the margin boundary of the region of interest and may be exterior to the region of interest. The region "RelDistanP" characterizes a set of prognostic parameters associated with the difference between a set of interior prognostic parameters less a set of prognostic parameters which may be associated with a classification of layers, which may be distant to the margin boundary of the region of interest and may be exterior to the region of interest.

Table 1 also shows exemplary fields for organizing prognostic parameters by various acoustic data types. In some embodiments, individual prognostic parameters may correspond to a statistical metric, such as mean or a standard-deviation, over a volume, such as defined by a region, a layer, or a classification of layers. Such data type may include but are not limited to, for example, the margin boundary score, the mean enhanced reflection (ErfMean), the relative mean of the enhanced reflection interior and exterior to the ROI (ErfRelDist), the standard deviation of the enhanced reflection (Erf_SD), the mean sound speed (SSMean), the relative mean sound speed interior and exterior to the ROI (SSRelDist), the standard deviation of the sound speed (SS_SD), the mean attenuation (AtMean), the standard deviation of the attenuation (At_SD), the mean of the attenuation corrected for the margin boundary score (Corr_At_Mean), and the standard deviation of the attenuation corrected for the margin boundary score (Corr_At_SD).

Classifier Model

At a step 770 of the method 700, a lesion within the volume of tissue may be characterized using the first plurality of interior prognostic parameters and the second plurality of exterior prognostic parameters. The prognostic parameters may be used within a classifier model in order to classify, predict, or otherwise characterize the region of interest. The analysis may predict whether the region of interest may be a cancerous mass, a benign fibroadenoma, a cyst, another benign finding, an unidentifiable mass (for example, there may be no finding), or any suitable characterization or classification. However, the analysis may additionally and/or alternatively monitor trends of one or more prognostic parameters over time, or for any suitable application. The step of analyzing the prognostic parameter may comprise the analysis of multiple prognostic parameters, which may be quantitative, semi-quantitative, qualitative, and/or extended.

Figure 9A:
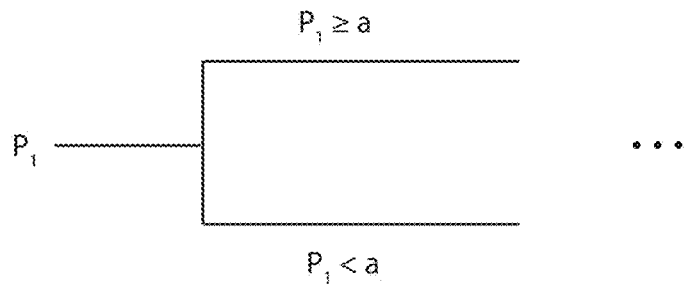
FIG. 9A shows an exemplary classifier model comprising a threshold value of a single prognostic parameter, in accordance with embodiments.

FIG. 9A shows an exemplary classifier model 910 comprising a threshold value of a single prognostic parameter, in accordance with embodiments. In some embodiments, prognostic parameter $P_1$ may be an extended prognostic parameter comprising a user-selected classification of a margin boundary of a region of interest according to an integer scale. In some embodiments, classifier model 910 may be based entirely upon qualitative or quantitative prognostic parameters associated with sound propagation in the volume of tissue. In other embodiments, classifier model 910 may be used in conjunction with another classifier model such as 920 or 930, such that the output of one classifier model may be used as a prognostic parameter in the input of another.

In some embodiments, the user-selected classification may be performed by a skilled operator, such as a medical professional, and in other embodiments, the user-selected classification may be aided by a computer implemented method or algorithm. In some embodiments, the classification may be performed in conjunction with observation of a waveform sound speed rendering; however, the classification may be performed using an image or rendering of any acoustic data type, such as the acoustic sound speed, acoustic attenuation, acoustic reflection, and an enhanced image generated from the sound speed, the acoustic attenuation, and the acoustic reflection.

In some embodiments, the user-selected classification may be assessed from an existing classification method such as the BI-RADS criteria, which may be predominantly devoted to assessment of tumor shape, margins and interaction with adjacent tissue. Such criteria as "shadowing" or "enhanced through transmission" in the BI-RADS may not be applicable ultrasound tomographic methods described herein; however, other criteria may be more sensitively detecting using ultrasound tomography, such as specular reflections of benign mass capsules, or the spiculations and/or architectural distortions of many cancers. In other embodiments, an adapted user-selected classification system may be implemented, which has been optimized for ultrasound tomographic imaging. Such a method may be based on a 5-point scale (the margin boundary score) that combines US-BI-RADS criteria for tumor margins as well as peritumoral tissue interaction.

An exemplary use of classifier model 910 includes a threshold for the operator assessed score at a value a, such that if $P_1 \geq a$ the mass may be diagnosed as cancerous. For example, Example 1 includes clinical data including diagnostic outcomes using the margin boundary score assessed from a waveform sound speed image for prognostic parameter $P_1$ and a threshold value of 3.

Another exemplary use of classifier model 910 includes a threshold for the operator assessed score at a value a, such that if $P_1 > a$ the mass may be diagnosed as cancerous. Another exemplary use of classifier model 910 includes a threshold for the operator assessed score at a value a, such that if $P_1 \leq a$ the mass may be diagnosed as cancerous. Another exemplary use of classifier model 910 includes a threshold for the operator assessed score at a value a, such that if $P_1 < a$ the mass may be diagnosed as cancerous. Another exemplary use of classifier model 910 includes evaluating a function of the value a and diagnosing the mass as cancerous based on the evaluated function of the value a.

Figure 9B:
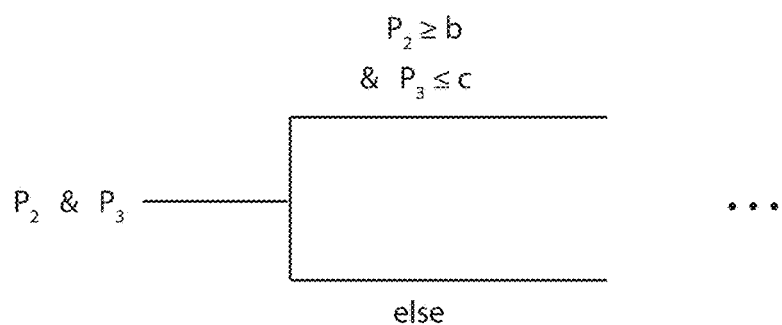
FIG. 9B shows an exemplary classifier model comprising a threshold value of an interior prognostic parameter and an exterior prognostic parameter, in accordance with embodiments.

FIG. 9B shows an exemplary classifier model 920 comprising a threshold value of an interior prognostic parameter and an exterior prognostic parameter, in accordance with embodiments. In some embodiments, classifier model 920 may be based entirely upon quantitative prognostic parameters associated with sound propagation in the volume of tissue. In other embodiments, classifier model 920 may be based upon a combination of quantitative, semi-quantitative, and/or extended prognostic parameters (e.g., a margin boundary score). In other embodiments, classifier model 920 may be used in conjunction with another classifier model such as 910 or 930 such that the output of one classifier model may be used as a prognostic parameter in the input of another.

An exemplary use of classifier model 920 includes a threshold for an interior prognostic parameter $P_2$ at a value b and an exterior prognostic parameter $P_3$ at a value c, such that if $P_2 \geq b$ and $P_3 \leq c$ the mass may be diagnosed as cancerous. For example, Example 1 includes clinical data including diagnostic outcomes using the volume-standard-deviation for the acoustic attenuation for prognostic parameter $P_2$ with a threshold value of 0.0347 and using the volume-average for the sound speed exterior to the region of interest (e.g., in the peritumoral region) for prognostic parameter $P_3$ with a threshold value of 1.51.

Another exemplary use of classifier model 920 includes a threshold for an interior prognostic parameter $P_2$ at a value b and an exterior prognostic parameter $P_3$ at a value c, such that if $P_2 > b$ and $P_3 > c$ the mass may be diagnosed as cancerous. Another exemplary use of classifier model 920 includes a threshold for an interior prognostic parameter $P_2$ at a value b and an exterior prognostic parameter $P_3$ at a value c, such that if $P_2 \leq b$ and $P_3 \leq c$ the mass may be diagnosed as cancerous. Another exemplary use of classifier model 920 includes a threshold for an interior prognostic parameter $P_2$ at a value b and an exterior prognostic parameter $P_3$ at a value c, such that if $P_2 < b$ and $P_3 < c$ the mass may be diagnosed as cancerous. Another exemplary use of classifier model 920 includes evaluating a function or piece-wise function of two or more variables (b, c, . . . ) and diagnosing the mass as cancerous based on the evaluated function of the two or more variables. For example, example 1 includes clinical data for diagnosing based upon a function of two variables, the volume-standard-deviation of the attenuation and the volume-standard-deviation of the sound speed in the tumoral region.

Figure 9C:
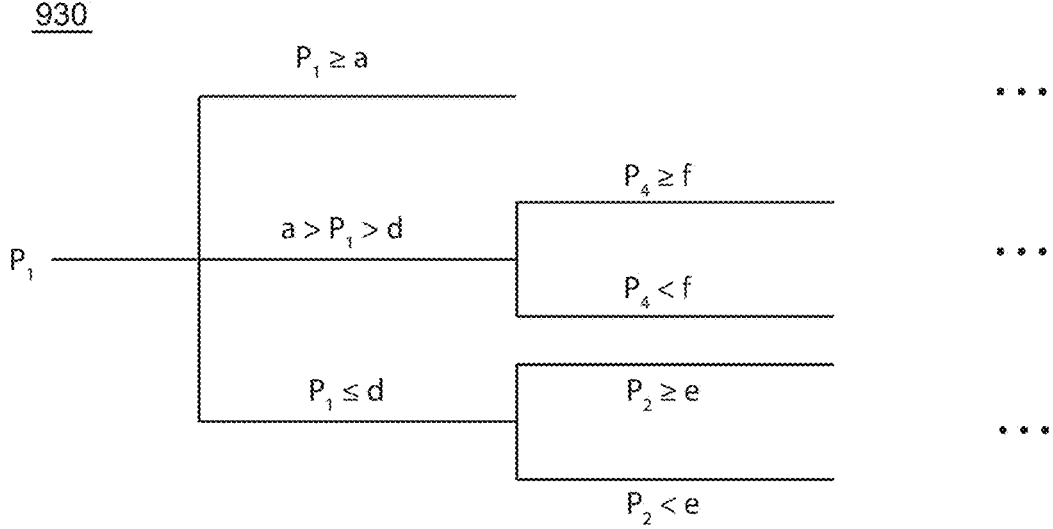
FIG. 9C shows an exemplary classifier model comprising a mixed qualitative and quantitative metric for assessing a mass, in accordance with embodiments.

FIG. 9C shows an exemplary classifier model 930 comprising a mixed qualitative and quantitative metric for assessing a mass, in accordance with embodiments. In some embodiments, classifier model 930 may be based entirely upon quantitative prognostic parameters associated with sound propagation in the volume of tissue. In other embodiments, classifier model 920 may be based upon a combination of quantitative, semi-quantitative, and/or extended prognostic parameters (e.g., a margin boundary score). In other embodiments, classifier model 930 may be used in conjunction with another classifier model such as 910 or 920 such that the output of one classifier model may be used as a prognostic parameter in the input of another.

An exemplary use of classifier model 930 includes: an operator assessed score $P_1$ with two threshold values at a and d; an interior prognostic parameter $P_2$ at a value e; and a relative prognostic parameter $P_4$ calculated from a difference of an interior and an exterior prognostic parameter at a value f. If the operator assessed score $P_1$ is greater than or equal to a, the mass may be characterized as cancerous. If the operator assessed score of the region of interest is greater than d and less than a, the relative prognostic parameter $P_4$ may be further included in the assessment. If the value of $P_4$ is greater than f the lesion may be characterized as cancerous. If the operator assessed score $P_1$ is less than or equal to d, interior prognostic parameter $P_2$ may be further included in the model. If the value of $P_2$ is greater than or equal to e the lesion may be classified as cancerous.

In the above use of classifier 930, $P_1$ may be the margin boundary score with thresholds at 2 and 4. If the value of $P_1$ is 3, $P_4$ may be a prognostic parameter corresponding to the volume-averaged enhanced reflectance in the tumoral region less the volume-averaged enhanced reflectance in the distant peritumoral region. If the difference is $\geq$ to −34.6, the mass may be assessed as cancerous. If the $P_1$ is 1 or 2, $P_3$ may be the volume-standard-deviation of the corrected acoustic attenuation in the region of interest. If the standard deviation is ≥0.15 the cancer may be diagnosed as cancerous. Though classifier models 910, 920, and 930 share prognostic parameters between models, the shared prognostic parameters shown are an example of one possible embodiment, and the exemplary prognostic parameters in each classifier model could be of any acoustic data type, such as those disclosed herein.

EXAMPLE 1

Clinical studies were conducted to develop a method of generating an enhanced image of a volume of tissue and a method for characterizing a volume of breast tissue of a patient. Results are presented from clinical studies that utilize breast imaging that is based on ultrasound tomography, which quantifies tissue characteristics while also producing 3-D images of breast anatomy, which methods described herein may include.

Informed consent was obtained from all patients, prospectively recruited in an IRB-approved protocol following HIPAA guidelines. Coronal images were produced by tomographic algorithms for reflection, sound speed and attenuation. All images were reviewed by a board-certified radiologist with more than 20 years of experience in breast imaging and US-technology development. In the first phase of the study, UST images were compared to multi-modal imaging to determine the appearance of lesions and breast parenchyma. In the second phase of the study, correlative comparisons with magnetic resonance (MR) breast imaging were used to establish basic operational capabilities of the ultrasound tomography (UST) system including the identification and characterization of parenchymal patterns, determination of the spatial resolution of UST and an estimate the breast volume that can imaged with UST. The third phase of the study focused on lesion characterization. Region of interest (ROI) analysis was performed on all identified lesions using all three UST image types. Combinations of the ROI generated values were used to characterize all masses in the study.

The studies demonstrated a high degree of correlation of breast tissue structures relative to fat subtracted contrast enhanced MRI and the ability to scan ~90% of the volume of the breast at a resolution of 0.7 mm in the coronal plane. With a scan duration of ~1-3 minutes, no significant motion artifacts were observed. Initial clinical results suggest an ability to characterize lesions using margin boundary scores in combination with sound speed and attenuation parameters.

Figure 10A:
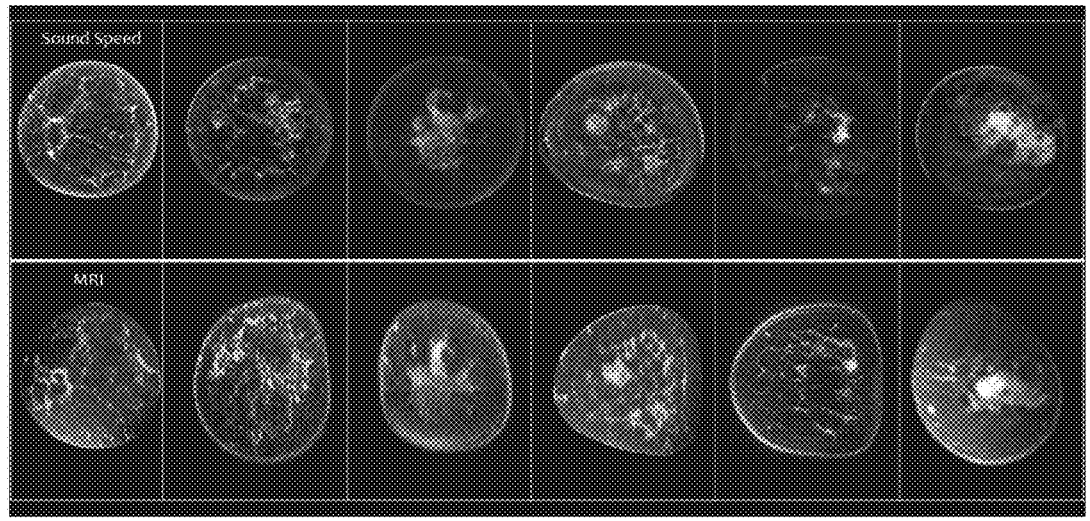
FIG. 10A shows a coronal view comparison between UST speed of sound and MR contrast enhanced fat subtracted images of representative breast parenchyma.

UST and MR imaging was performed within weeks of each other. UST imaging was carried out with the SoftVue system (Delphinus Medical Technologies) and the MR exams with a Philips Achieva 3T system. The resulting image sequences were qualitatively and quantitatively to assess imaging performance of UST. As discussed above, UST images correlate best with MR images. Further inspection shows that of the three UST image types, the sound speed image correlates best with MR. FIG. 10A shows a coronal view comparison between UST speed of sound and MR contrast enhanced fat subtracted images of representative breast parenchyma.

The parenchymal patterns are very similar with the only major difference relating to the shape of the breast. This difference can be explained by the fact that the SoftVue system utilizes water so that buoyancy foreshortens the breast while with MR, gravity lengthens the breast in the AP dimension (e.g., prone). As discussed above, UST images correlate best with MR images. Further inspection shows that of the three UST image types, the sound speed image correlates best with MR, as illustrated in FIG. 10A.

MRI and UST breast volumes were compared using a paired t-test. In the first step, a k-means segmentation algorithm was applied to $T_1$ breast MR images to automatically separate out the non-tissue background. In the second step, the boundary between the breast tissue and the chest wall was drawn manually and the chest wall removed, leaving behind only breast tissue.

In the UST images a semi-automated tool was used to draw a boundary around the breast tissue in each coronal slice and everything outside the boundary removed (water signal). Any slices containing chest wall signal were also removed.

Figure 10B:
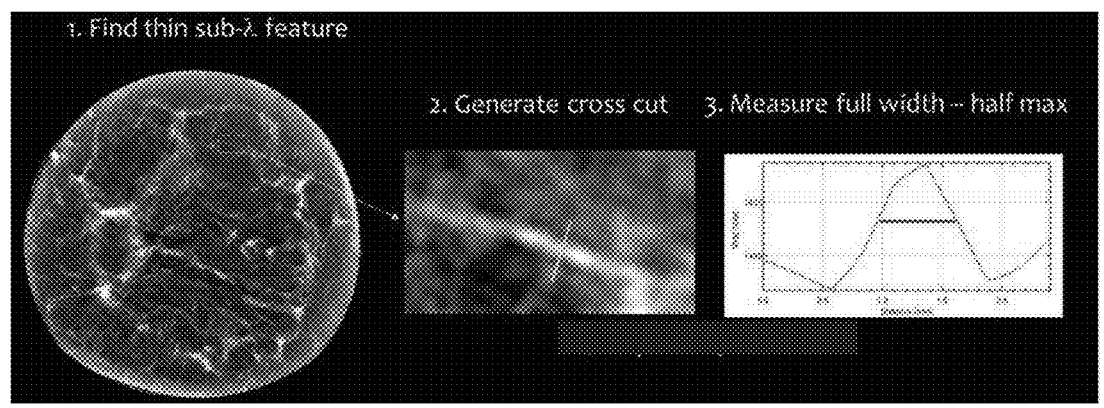
FIG. 10B shows profile cuts of thin features using, the full-width, half-maximum criterion to estimate the spatial resolution of each modality.

The spatial resolution of each modality was estimated using profile cuts of thin features, using the full-width, half-maximum criterion as shown in FIG. 10B. The results of the spatial resolution analysis are shown in the table below. The spatial resolution was found to be dependent on the reprojection type for both MRI and with UST outperforming MRI in the coronal plane and MRI outperforming UST in the other projections. (However, MR acquisitions with isotropic voxels would show comparable resolution to UST in the coronal plane). The UST image voxels are not isotropic and data acquisition cannot be readily adjusted like MR, such that UST reconstructed in axial and sagittal planes have resolution that approach the 2.5-mm slice thickness at this time.

| Resolution | UST | MRI |
| --- | --- | --- |
| Coronal | 0.7 +/− 0.1 mm | 1.6 +/− 0.3 mm |
| Axial/Sagittal | 2.5 +/− 0.5 mm | 0.8 +/− 0.1 mm |

US-BI-RADS criteria are predominantly devoted to assessment of tumor shape, margins, and interaction with adjacent tissue. However, criteria such as shadowing or enhanced through transmission are not applicable to UST's circular geometry. In addition, UST, operating at 3 MHz, appears more sensitive to the specular reflectors of benign mass capsules, or the spiculations and/or architectural distortions of many cancers. Therefore, we developed a 5-point scale (the margin boundary score) that combined US-BI-RADS criteria for tumor margins, as well as possibilities for peritumoral tissue interaction.

Figure 11:
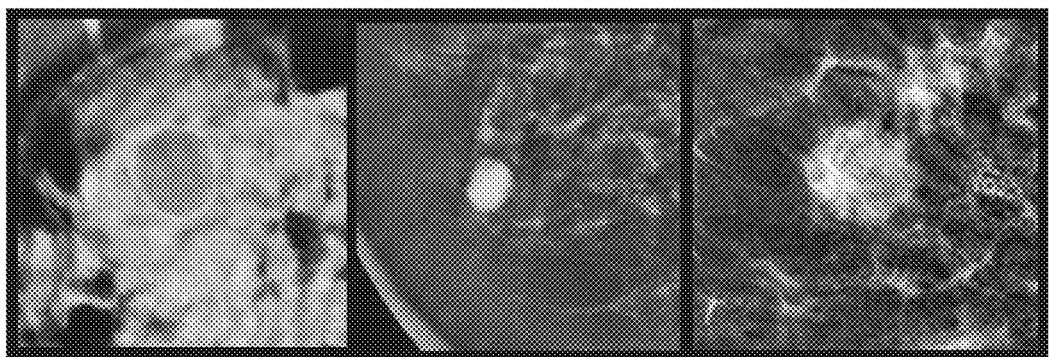
FIG. 11 shows the basic differences in sound speed texture and morphology noted for many cysts, fibroadenomas and cancer.

An ultimate goal may be to generate textural analyses that may be less operator dependent and serve as appropriate diagnostic aids for a detected mass by simply requiring the radiologist to draw an ellipsoidal ROI. FIG. 11 shows the basic differences in sound speed texture and morphology noted for many cysts, fibroadenomas, and cancer. Based on the margin boundary score's five point scale, a classifier model can be implemented using classifier model 910, wherein a margin boundary score equal to or above a threshold value of three may be diagnosed as cancer. A first table showing the type of lesion, the assessed margin boundary score of the region for the patients surveyed (containing 107 benign lesions and 31 cancers) is shown below:

| SS Margin Boundary | Cancer | Fibro | Cyst | Benign |
| --- | --- | --- | --- | --- |
| 1 | 2 | 32 | 26 | 2 |
| 2 | 1 | 16 | 11 | 8 |
| 3 | 6 | 5 | 3 | 3 |
| 4 | 19 | 0 | 0 | 1 |
| 5 | 3 | 0 | 0 | 0 |
| Total | 31 | 53 | 40 | 41 |

A second summary table showing the diagnostic results is shown below:

| | | | |
| --- | --- | --- | --- |
| Sensitivity | 90% | Total Positive | 28 |
| Specificity | 88.8% | False Positive | 12 |
| PPV | 70% | Total Negative | 95 |
| NPV | 96.9% | False Negative | 3 |
| Accuracy | 90.3% | Total | 138 |

Additionally, masses were characterized by a (i) Margin Boundary score, (ii) reflectivity, (iii) quantitative SS evaluation, and (iv) ATT evaluations. A semi-automatic Region-of-interest (ROI) tool was used to determine the quantitative properties of each mass. After identifying the mass of interest, a simple elliptical ROI may be drawn around the mass. The ROI algorithm then generates 20 radial ellipsoids—10 inside and 10 outside the mass. Quantitative information was then measured for each of the 20 annuli for subsequent analysis. The region of interest (ROI) analysis was performed on all identified lesions using all three UST image types. Combinations of the ROI generated values were used to characterize all masses in the study.

Figure 12A:
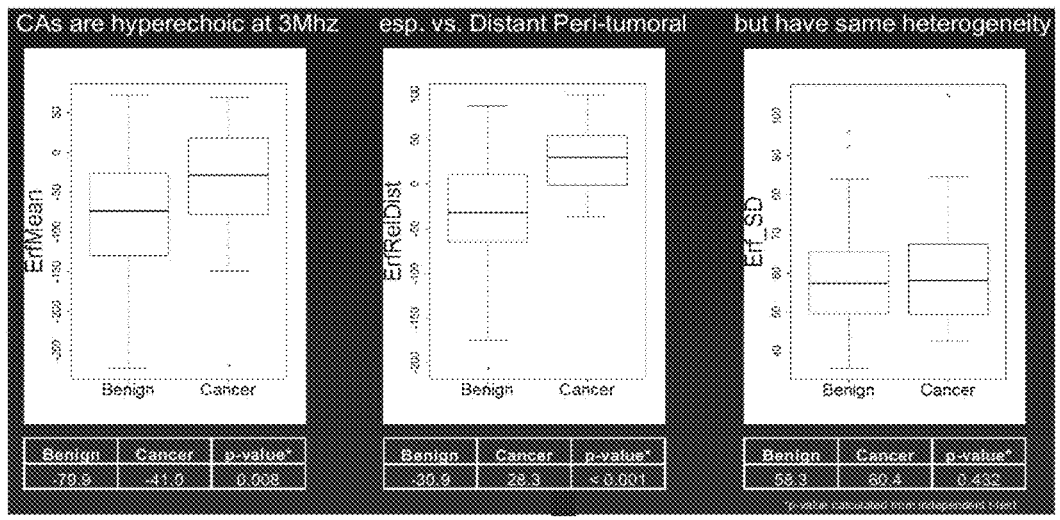
FIG. 12A shows box plots summarizing first-order sound reflection statistics within the tumoral ROI and comparisons with the surrounding peritumoral region.
Figure 12B:
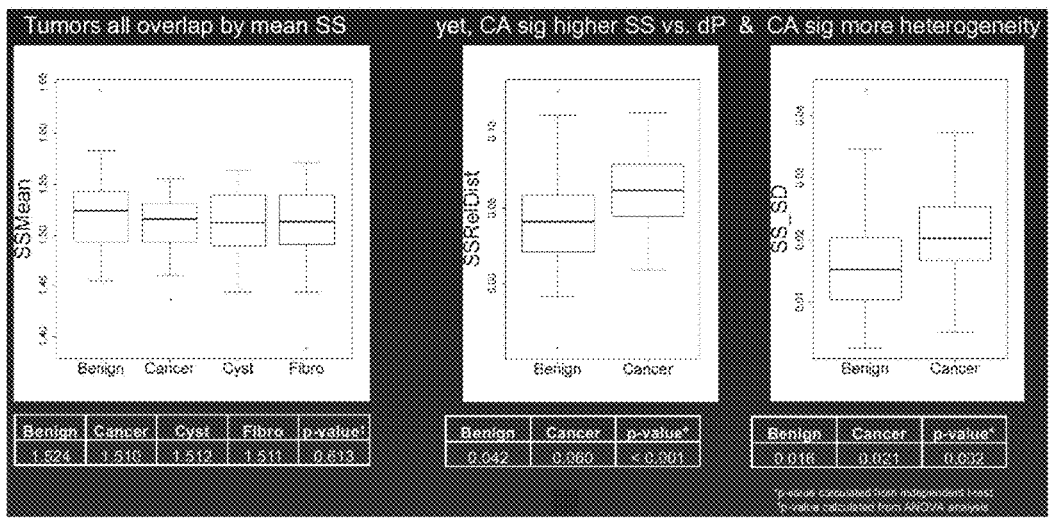
FIG. 12B shows box plots summarizing first-order sound speed statistics within the tumoral ROI and comparisons with the surrounding peritumoral region.
Figure 12C:
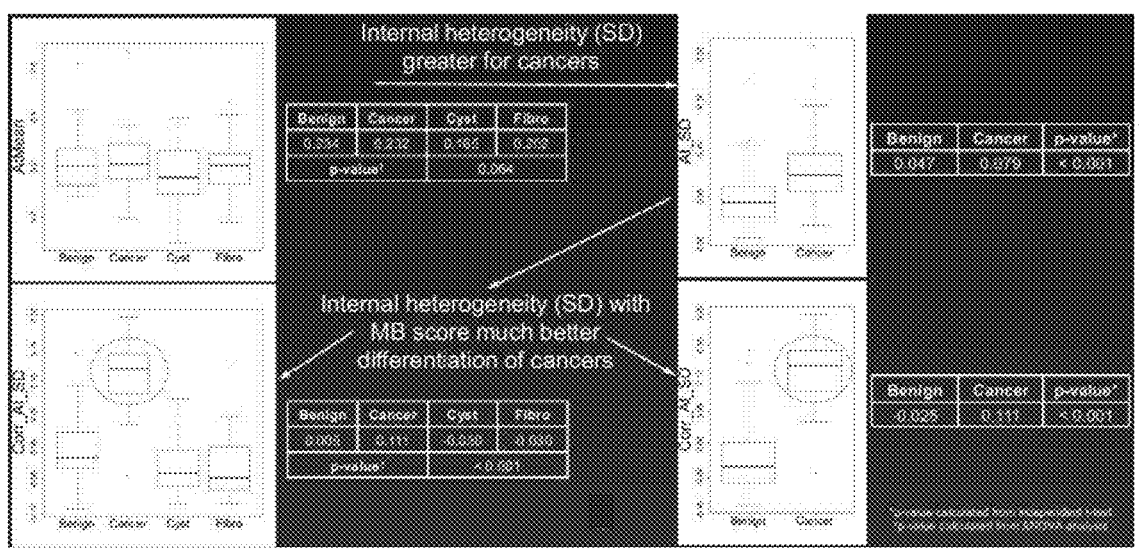
FIG. 12C shows box plots summarizing first-order attenuation statistics within the tumoral ROI and comparisons with the surrounding peritumoral region.

Our recent data highlights the significant impacts of first-order statistics, such as standard deviation, within the tumoral ROI and comparisons with the surrounding peritumoral region. FIGS. 12A-12C show box plots summarizing said first order statistics including: the mean enhanced reflection (ErfMean), the relative mean enhanced reflection interior and exterior to the ROI (ErfRelDist), the standard deviation of the enhanced reflection (Erf_SD), the mean sound speed (SSMean), the relative mean sound speed interior and exterior to the ROI (SSRelDist), the standard deviation of the sound speed (SS_SD), the mean attenuation (AtMean), the standard deviation of the attenuation (At_SD), and the standard deviation of the attenuation corrected for the margin boundary score (Corr_At_SD). Each box plot also contains a summary table showing the associated value of the statistic for various types of lesions. The box plots were based on taking the average values for 107 benign lesions and 31 cancers.

Scatterplots and box plots of the optimal methods were used to illustrate the characterization potential. The box plot in FIG. 12C shows the differentiation achieved when using the boundary score combined with the first-order statistic of standard deviation, a more crude measure of heterogeneity, based upon tumoral ROI extracted from ATT images, which had only slightly higher significance than SS. These ROIs were again obtained by simply drawing an elliptical ROI around the mass and determining the standard deviation with in the ROI.

Figure 13A:
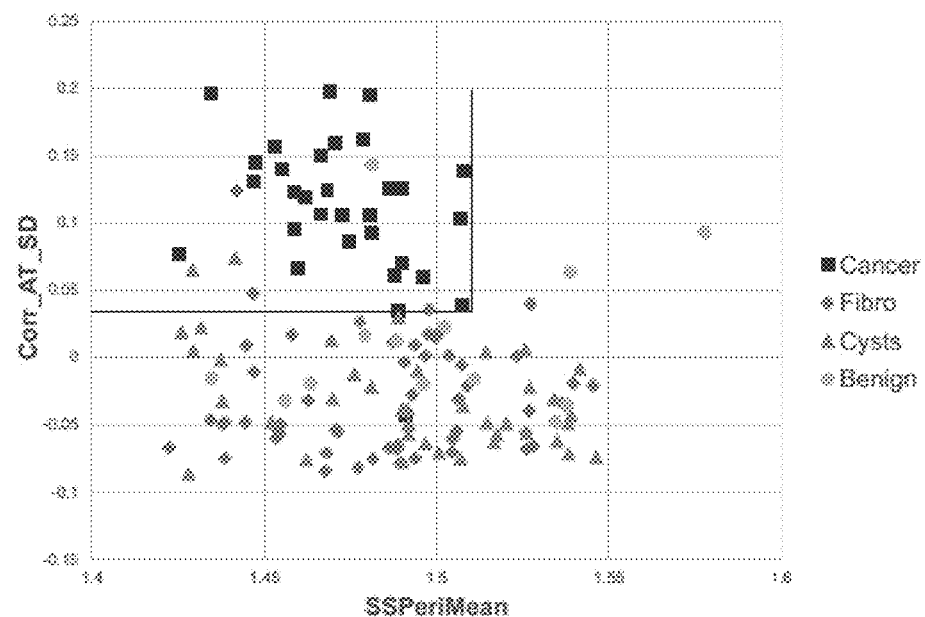
FIG. 13A shows a scatter plot based on the mean sound speed of the peritumoral mass region and the standard deviation of the attenuation within the tumor.

Upon further investigation, it was found that the SS of the peritumoral mass region (defined by an annular area just outside the mass boundary ROI) further separated the benign masses from cancer. The following data is generated using classifier method 920. A scatter plot based on all of these parameters is shown in FIG. 13A. The scatter plot shows separately the cancers, fibroadenomas and cancers. The cancers are tightly grouped in the top left corner of the plot indicating high boundary scores, high heterogeneity (standard deviation of sound attenutation≥0.0347) and lower peritumoral sound speed (mean sound speed in the peritumoral region≤1.51). By these measures, there was not much separation between cysts and fibroadenomas but significant separation between them and cancer. ROC analysis of the data represented in the scatter plot indicates a PPV of 91% when the sensitivity is 97%. A summary table showing the results is shown below:

| Sensitivity | 97% | Total Positive | 30 |
| Specificity | 94.4% | False Positive | 6 |
| PPV | 83% | Total Negative | 101 |
| NPV | 99.0% | False Negative | 1 |
| Accuracy | 96.8% | Total | 138 |

Figure 13B:
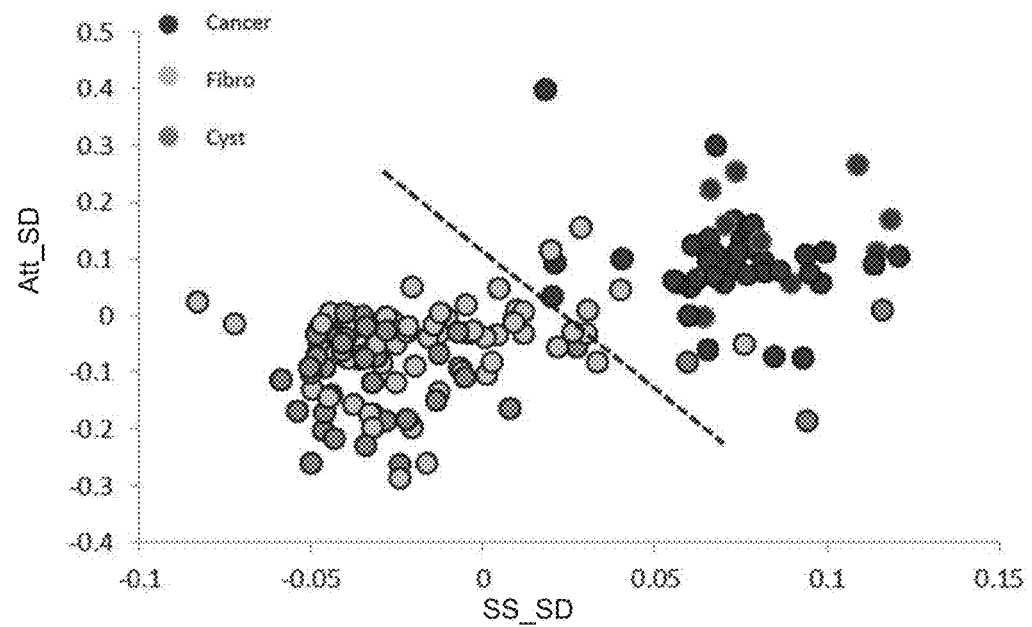
FIG. 13B shows a scatter plot based on the standard-deviation of the sound speed within the tumor and the standard-deviation of the attenuation within the tumor.

FIG. 13B shows a scatter plot based on the standard-deviation of the sound speed within the tumor and the standard-deviation of the attenuation within the tumor. An illustrative example of classifier model 920 using a linear function of the two prognostic parameters is shown by the line drawn through the scatter plot. If patient values for each of the two prognostic parameters plotted in FIG. 13B are above and right of the line, the lesion is diagnosed as cancerous.

This is a subset of data relative to an expanded ongoing study that includes more quantitative margin analyses. This method can also serve as a teaching tool for identifying grossly apparent textural differences within the tumor and surrounding peritumoral region.

Ultrasound Tomography System

FIGS. 2A-C show a schematic of an exemplary ultrasound scanner, a schematic of a patient breast in an exemplary ultrasound scanner, and a schematic of an exemplary ultrasound transducer of an ultrasound scanner, respectively, in accordance with embodiments. As shown in FIGS. 2A-C, an ultrasound tomography scanner 200 may comprise a transducer 220 configured to receive the volume of tissue and comprising an array of ultrasound transmitters 224 and an array of ultrasound receivers 226. The array of ultrasound transmitters may be configured to emit acoustic waveforms toward the volume of tissue, and the array of ultrasound receivers 226 may be configured to detect a set of acoustic signals derived from acoustic waveforms transmitted through the volume of tissue The ultrasound tomography scanner 200 may further comprise a computer 210 in communication with the transducer, comprising one or more processors and non-transitory computer-readable media with instructions stored thereon that when executed may be configured to perform the methods of generating an enhanced image of a volume of tissue, the methods of characterizing a volume of breast tissue, and embodiments and variations described herein. The ultrasound tomography scanner 200 may further comprise a display 290 in communication with the digital processing device 210 and configured to render the enhanced image of the volume of tissue.

The system 200 functions to render ultrasound images and/or generate transformed ultrasound data that may be used to generate a high resolution image of structures present within a volume of tissue. In some embodiments, the system 200 may function to produce images that may be aligned with regulatory standards for medical imaging, as regulated, for instance, by the U.S. Food and Drug Administration (FDA). The system 200 may be configured to implement at least a portion of an embodiment, variation, or example of method 100 described above; however, the system 200 may additionally or alternatively be configured to implement any other suitable method.

The transducer 220, the computer processor 210, and the display 290 may be coupled to a scanner table 205, as shown in FIGS. 2A and 2B, wherein the scanner table 205 has an opening 206 that provides access to the volume of tissue of the patient. The table, which may be made of a durable, flexible material (e.g., flexible membrane, fabric, etc.), may contour to the patient's body, thereby increasing scanning access to the axilla regions of the breast and increasing patient comfort. The opening 206 in the table may allow the breast (or other appendage) to protrude through the table and be submerged in an imaging tank 230 filled with water or another suitable fluid as an acoustic coupling medium that propagates acoustic waves.

FIGS. 2B and 2C show a schematic of a patient breast in an exemplary ultrasound scanner and a schematic of an exemplary ultrasound transducer of an ultrasound scanner, in accordance with embodiments. As shown in FIGS. 2B and 2C, a ring-shaped transducer 220 with transducer elements 222 may be located within the imaging tank 230 and encircle or otherwise surround the breast, wherein each of the transducer elements 222 may comprise one of the array of ultrasound transmitters 224 paired with one of the array of ultrasound receivers 226. Multiple ultrasound transmitters 224 that direct safe, non-ionizing ultrasound pulses toward the tissue and multiple ultrasound receivers 226 that receive and record acoustic signals scattering from the tissue and/or transmitted through the tissue may be distributed around the ring transducer 220. In one embodiment, transducer 220 may be organized such that each ultrasound transmitter element may be paired with a corresponding ultrasound receiver element, each ultrasound transmitter element may be surrounded by two adjacent ultrasound transmitter elements, each ultrasound receiver element may be surrounded by two adjacent ultrasound receiver elements, and the transducer may be axially symmetric, as in FIG. 2C.

During the scan, the ring transducer 220 may pass along the tissue, such as in an anterior-posterior direction between the chest wall and the nipple region of the breast to acquire an acoustic data set including measurements such as acoustic reflection, acoustic attenuation, and sound speed. The data set may be acquired at discrete scanning steps, or coronal "slices". The transducer 220 may be configured to scan step-wise in increments from the chest wall towards the nipple, and/or from the nipple towards the chest wall. However, the transducer 220 may additionally and/or alternatively receive data regarding any suitable biomechanical property of the tissue during the scan, and in any suitable direction.

In some embodiments, the scanner table may comprise an embodiment, variation, or example of the patient interface system described in any of the references incorporated herein. However, system 200 may additionally or alternatively comprise or be coupled with any other suitable patient interface system.

Digital Processing Device

In some embodiments, the platforms, systems, media, and methods described herein include a digital processing device, or use of the same. In further embodiments, the digital processing device includes one or more hardware central processing units (CPUs), general purpose graphics processing units (GPGPUs), or field programmable gate arrays (FPGAs) that carry out the device's functions. In still further embodiments, the digital processing device further comprises an operating system configured to perform executable instructions. In some embodiments, the digital processing device may be optionally connected a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, set-top computers, media streaming devices, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

In some embodiments, the digital processing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®. Those of skill in the art will also recognize that suitable media streaming device operating systems include, by way of non-limiting examples, Apple TV®, Roku®, Boxee®, Google TV®, Google Chromecast®, Amazon Fire®, and Samsung® HomeSync®. Those of skill in the art will also recognize that suitable video game console operating systems include, by way of non-limiting examples, Sony® PS3®, Sony® PS4®, Microsoft® Xbox 360®, Microsoft Xbox One, Nintendo® Wii®, Nintendo® Wii U®, and Ouya®.

In some embodiments, the device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

In some embodiments, the digital processing device includes a display to send visual information to a user. In some embodiments, the display is a cathode ray tube (CRT). In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In still further embodiments, the display is a combination of devices such as those disclosed herein.

In some embodiments, the digital processing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera or other sensor to capture motion or visual input. In further embodiments, the input device is a Kinect, Leap Motion, or the like. In still further embodiments, the input device is a combination of devices such as those disclosed herein.

Figure 14:
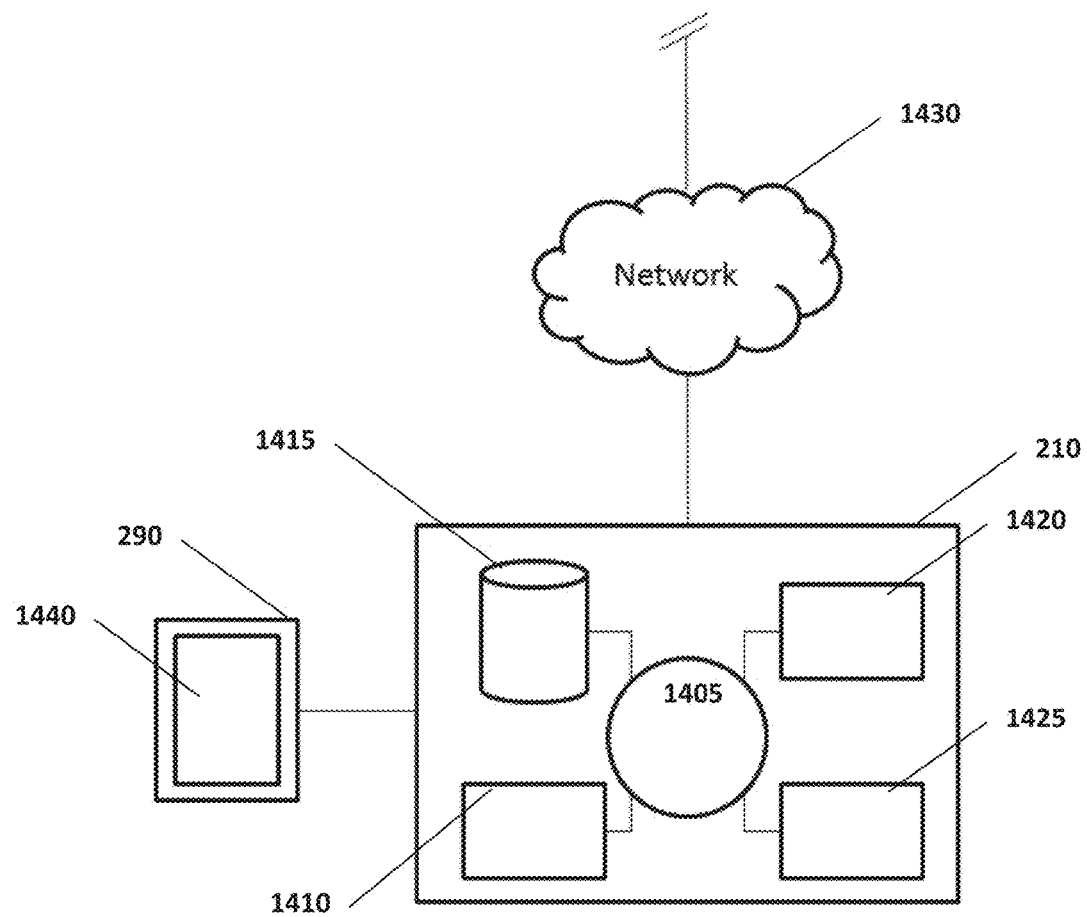
FIG. 14 shows a computer control system that is programmed or otherwise configured to implement methods provided herein.

Referring to FIG. 14, in a particular embodiment, an exemplary digital processing device 210 is programmed with instructions or otherwise configured to implement the method of generating an enhanced image of a volume of tissue and the method for characterizing a volume of breast tissue of a patient, as described herein. The device 210 may regulate various aspects of the ultrasound tomography system, imaging methods, and characterizing methods of the present disclosure, such as, for example, performing processing steps. In this embodiment, the digital processing device 210 includes a central processing unit (CPU, also "processor" and "computer processor" herein) 1405, which can be a single core or multi core processor, or a plurality of processors for parallel processing. The digital processing device 210 also includes memory or memory location 1410 (e.g., random-access memory, read-only memory, flash memory), electronic storage unit 1415 (e.g., hard disk), communication interface 1420 (e.g., network adapter) for communicating with one or more other systems, and peripheral devices 1425, such as cache, other memory, data storage and/or electronic display adapters. The memory 1410, storage unit 1415, interface 1420 and peripheral devices 1425 are in communication with the CPU 1405 through a communication bus (solid lines), such as a motherboard. The storage unit 1415 can be a data storage unit (or data repository) for storing data. The digital processing device 210 can be operatively coupled to a computer network ("network") 1430 with the aid of the communication interface 1420. The network 1430 can be the Internet, an internet and/or extranet, or an intranet and/or extranet that is in communication with the Internet. The network 1430 in some cases is a telecommunication and/or data network. The network 1430 can include one or more computer servers, which can enable distributed computing, such as cloud computing. The network 1430, in some cases with the aid of the device 210, can implement a peer-to-peer network, which may enable devices coupled to the device 210 to behave as a client or a server.

Continuing to refer to FIG. 14, the CPU 1405 can execute a sequence of machine-readable instructions, which can be embodied in a program or software. The instructions may be stored in a memory location, such as the memory 1410. The instructions can be directed to the CPU 1405, which can subsequently program or otherwise configure the CPU 1405 to implement methods of the present disclosure. Examples of operations performed by the CPU 1405 can include fetch, decode, execute, and write back. The CPU 1405 can be part of a circuit, such as an integrated circuit. One or more other components of the device 210 can be included in the circuit. In some cases, the circuit is an application specific integrated circuit (ASIC) or a field programmable gate array (FPGA).

Continuing to refer to FIG. 14, the storage unit 1415 can store files, such as drivers, libraries and saved programs. The storage unit 1415 can store user data, e.g., user preferences and user programs. The digital processing device 210 in some cases can include one or more additional data storage units that are external, such as located on a remote server that is in communication through an intranet or the Internet.

Continuing to refer to FIG. 14, the digital processing device 210 can communicate with one or more remote computer systems through the network 1430. For instance, the device 210 can communicate with a remote computer system of a user. Examples of remote computer systems include personal computers (e.g., portable PC), slate or tablet PCs (e.g., Apple® iPad, Samsung® Galaxy Tab), telephones, Smart phones (e.g., Apple® iPhone, Android-enabled device, Blackberry®), or personal digital assistants.

Methods as described herein can be implemented by way of machine (e.g., computer processor) executable code stored on an electronic storage location of the digital processing device 210, such as, for example, on the memory 1410 or electronic storage unit 1415. The machine executable or machine readable code can be provided in the form of software. During use, the code can be executed by the processor 1405. In some cases, the code can be retrieved from the storage unit 1415 and stored on the memory 1410 for ready access by the processor 1405. In some situations, the electronic storage unit 1415 can be precluded, and machine-executable instructions are stored on memory 1410.

The digital processing device 210 can include or be in communication with an electronic display 290 that comprises a user interface (UI) 1440. Examples of UI's include, without limitation, a graphical user interface (GUI) and web-based user interface. In some cases, electronic display 290 may be connected to the computer system 210 via a network, e.g., via network 1430.

Non-Transitory Computer Readable Storage Medium

In some embodiments, the platforms, systems, media, and methods disclosed herein include one or more non-transitory computer readable storage media encoded with a program including instructions executable by the operating system of an optionally networked digital processing device. In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

Computer Program

In some embodiments, the platforms, systems, media, and methods disclosed herein include at least one computer program, or use of the same. A computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

In some embodiments, a computer program includes a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB .NET, or combinations thereof. Compilation is often performed, at least in part, to create an executable program. In some embodiments, a computer program includes one or more executable complied applications.

In some embodiments, the platforms, systems, media, and methods disclosed herein include software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

In some embodiments, the platforms, systems, media, and methods disclosed herein include one or more databases, or use of the same. In view of the disclosure provided herein, those of skill in the art will recognize that many databases are suitable for storage and retrieval of information. In various embodiments, suitable databases include, by way of non-limiting examples, relational databases, non-relational databases, object oriented databases, object databases, entity-relationship model databases, associative databases, and XML databases. Further non-limiting examples include SQL, PostgreSQL, MySQL, Oracle, DB2, and Sybase. In some embodiments, a database is internet-based. In further embodiments, a database is web-based. In still further embodiments, a database is cloud computing-based. In other embodiments, a database is based on one or more local computer storage devices While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for generating an enhanced image of a volume of tissue, which method is implemented by a computer comprising one or more processors and computer readable media comprising instructions, the method comprising:
receiving from a transducer, a plurality of acoustic signals derived from acoustic waveforms transmitted through the volume of tissue, wherein the transducer comprises an array of ultrasound transmitters and an array of ultrasound receivers configured to surround the volume of tissue;
generating from the plurality of acoustic signals a first reflection rendering comprising a first distribution of reflection values across a region of the volume of tissue;
generating from the plurality of acoustic signals a sound speed rendering comprising a distribution of sound speed values across the region of the volume of tissue;
calculating a second reflection rendering from the sound speed rendering, the second reflection rendering comprising a second distribution of reflection values across the region of the volume of tissue; and
generating an enhanced image of the volume of tissue by rendering one or more combined images of the first reflection rendering and the second reflection rendering.

2. The method of claim 1, wherein the tissue comprises breast tissue.

3. The method of claim 1, wherein the volume of tissue comprises a distribution of one or more of: fat tissue, parenchymal tissue, cancerous tissue, and abnormal tissue.

4. The method of claim 3, wherein the fat tissue comprises fatty parenchyma, parenchymal fat, or subcutaneous fat.

5. The method of claim 3, wherein the abnormal tissue comprises fibrocystic tissue or a fibroadenoma.

6. The method of claim 1, wherein generating the first reflection rendering comprises generating a plurality of acoustomechanical parameter slices associated with a plurality of coronal slices through the volume of tissue.

7. The method of claim 1, wherein generating the first reflection rendering comprises generating a distribution of acoustic reflection signals, wherein the acoustic reflection signals characterize a relationship between reflected intensities and emitted intensities of the acoustic waveforms, wherein the relationship is selected from the group consisting of a sum, a difference, and a ratio.

8. The method of claim 1, wherein generating the first reflection rendering comprises generating a distribution of acoustic reflection signals, wherein the acoustic reflection signals characterize a change in acoustic impedance of the volume of tissue.

9. The method of claim 1, wherein generating the first reflection rendering comprises generating a distribution of acoustic reflection signals received from a first array of transducers, the first array of transducers transmitting and receiving at a first frequency greater than a second frequency of a second array of transducers used to generate the sound speed rendering.

10. The method of claim 1, wherein generating the first reflection rendering comprises generating a distribution of acoustic reflection signals received from a first array of transducers, the first array of transducers transmitting and receiving at a first frequency less than a second frequency of a second array of transducers used to generate the sound speed rendering.

11. The method of claim 1, wherein generating the sound speed rendering comprises generating a plurality of acoustomechanical parameter slices associated with a plurality of coronal slices through the volume of tissue.

12. The method of claim 1, wherein the sound speed rendering is complex-valued and comprises a real portion corresponding to a sound speed, and an imaginary portion corresponding to a sound attenuation.

13. The method of claim 1, wherein generating the sound speed rendering comprises generating an initial sound speed rendering based on simulated waveforms according to a time travel tomography algorithm, and wherein the initial sound speed rendering is iteratively optimized until ray artifacts are reduced to a threshold.

14. The method of claim 13, wherein the simulated waveforms are optimized for each of a plurality of sound frequency components.

15. The method of claim 1, wherein generating the second reflection rendering comprises calculating a gradient of the sound speed rendering.

16. The method of claim 15, wherein calculating the gradient comprises performing one or more algorithms selected from the group consisting of the Sobel-Feldman operator, the Scharr operator, the Prewitt operator, and the Roberts Cross operator.

17. The method of claim 15, wherein calculating generating a second reflection rendering comprises performing computational relations selected from the group consisting of averaging, truncation, normalization, smoothing, addition, subtraction, multiplication, and division.

18. The method of claim 17, wherein smoothing comprises convolution with another function, adjacent averaging, or Fourier filtering.

19. The method of claim 1, wherein rendering the one or more combined images comprises performing an element-wise average or a weighted average of the first reflection rendering and the second reflection rendering.

20. The method claim 19, wherein rendering the one or more combined images comprises performing computational relations on the first reflection rendering or the second reflection rendering, the computational relations selected from the group consisting of averaging, truncation, normalization, smoothing, addition, subtraction, multiplication, and division.

21. The method of claim 1, wherein rendering the one or more combined images comprises performing an element-wise sum or a weighted sum of the first reflection rendering and the second reflection rendering.

22. The method of claim 21, wherein rendering the one or more combined images comprises performing computational relations on the first reflection rendering or the second reflection rendering, the computational relations selected from the group consisting of averaging, truncation, normalization, smoothing, addition, subtraction, multiplication, and division.

23. The method of claim 1, wherein rendering the one or more combined images comprises performing an element-wise product or a weighted product of the first reflection rendering and the second reflection rendering.

24. The method of claim 23, wherein rendering the one or more combined images comprises performing computational relations on the first reflection rendering or the second reflection rendering, the computational relations selected from the group consisting of averaging, truncation, normalization, smoothing, addition, subtraction, multiplication, and division.

25. The method of claim 1, wherein rendering the one or more combined images comprises performing a convolution of the first reflection rendering and the second reflection rendering.

26. The method of claim 25, wherein rendering the one or more combined images comprises performing computational relations on the first reflection rendering or the second reflection rendering, the computational relations selected from the group consisting of averaging, truncation, normalization, smoothing, addition, subtraction, multiplication, and division.

27. The method of claim 1, further comprising classifying, based on the one or more combined images, different types of lesions in the volume of tissue as at least one of a cancerous tumor, a fibroadenoma, a cyst, a nonspecific benign mass, and an unidentifiable mass.

28. A non-transitory computer-readable storage medium with instructions stored thereon that, when executed by a processor, cause a processor to perform the method of claim 1.

* * * * *